US006989362B1

(12) United States Patent
Bibb et al.

(10) Patent No.: US 6,989,362 B1
(45) Date of Patent: Jan. 24, 2006

(54) METHODS OF TREATING DOPAMINE DYSREGULATION USING AGENTS THAT REGULATE PHOSPHORYLATION/DEPHOSPHORYLATION IN DOPAMINE SIGNALING

(75) Inventors: James A. Bibb, New York, NY (US); Paul Greengard, New York, NY (US)

(73) Assignee: The Rockefeller University, New York, NY (US)

(*) Notice: Subject to any disclaimer, the term of this patent is extended or adjusted under 35 U.S.C. 154(b) by 264 days.

(21) Appl. No.: 09/687,959

(22) Filed: Oct. 13, 2000

Related U.S. Application Data

(63) Continuation-in-part of application No. 09/419,379, filed on Oct. 15, 1999, now abandoned.

(51) Int. Cl.
*A61K 31/77* (2006.01)
*A61K 31/40* (2006.01)
*A61K 31/407* (2006.01)
*A61P 25/14* (2006.01)
*A61P 25/16* (2006.01)
*C07D 487/02* (2006.01)

(52) U.S. Cl. ............................ 514/1; 514/415; 514/43; 514/411; 424/78.38; 548/484

(58) Field of Classification Search .................... 514/1, 514/43, 415, 411, 2; 424/78.38; 548/484
See application file for complete search history.

(56) References Cited

U.S. PATENT DOCUMENTS 5,777,195 A 7/1998 Fienberg et al. ............... 800/2
6,013,621 A 1/2000 Nishi et al. .................... 514/2

FOREIGN PATENT DOCUMENTS

WO WO 99/20273 4/1999

OTHER PUBLICATIONS

Greengard The neurobiolgy of slow synaptic transmission vol. 294 Nov. 2, 2001.*
Jaber et al. Dopamine receptors and brain function pp. 1503–1519 Jun. 12, 1996.*
Ahuja et al., 1997, Developmental Genetics, 21:258–67.
Altucci et al., 1997, Endocrinology, 138:978–984.
Ando et al., 1997, J. Biochem, 122:409–414.
Backstrom et al., 1998, Society for Neuroscience, 24:284 Article No. 116.3.
Besset et al., 1998, Molecular Reproduction and Development, 50:18–29.
Cai et al., 1997, Neurosci Res, 28:355–60.
Chang et al., 1999, Chemistry & Biology, 6:361–75.
Chin et al., 1999, The Journal of Biological Chemistry, 274:7120–7127.
Chou et al., 1999, Biochemical and Biophysical Research Communications, 259:420–28.
Delalle t al., 1997, Journal of Neurocytology, 26:283–296.
Fienberg et al., 1998, Science, 281:838–842.
Filgueira d Azevedo, Jr. et al., 1996, Biochemistry, 93:2735–2740.
Fletcher et al., 1999, The Journal of Biological Chemistry, 274:4027–4035.
Gervasi and Szaro, 1995, Molecular Brain Research, 33: 192–200.
Girault et al., 1989, The Journal of Biological Chemistry, 264:21748–21759.
Gray et al., 1998, Current Opinion in Neurobiology, 8:330–334.
Green et al., 1997, Neurochem., 31:617–623.
Guidato et al., 1998, J. Neurochem., 70:335–340.
Hasegawa et al., 1996, Neurochem., 28:221–229.
Hellmich et al., 1992, Neurobiology, 89:10867–10871.
Hemmings, Jr. et al., 1989, The Journal of Biological Chemistry, 264:7726–7733.
Hemmings, Jr. et al., 1984, Nature, 310:7726–7733.
Henchcliffe and Burke, 1997, Neuroscience Letter, 230:41–44.
Hisanaga et al., 1993, The Journal of Biological Chemistry, 268:15056–15060.
Horiuchi et al., 1990, The Journal of Biological Chemistry, 265:9476–9484.
Hosoi et al., 1995, J. Biochem, 117:741–749.
Ino and Chiba, 1996, Brain Research, 732:170–185.
Iseki et al., 1997, Surgery, 122:187–195.
Ishiguro et al., 1994, FEBS Letters, 342:203–208.
Ishiguro et al., 1995, Neuroscience Letters, 202:81–84.
Ishizuka et al., 1995, Gene, 166:267–271.
Klauck et al., 1996, Science, 271:1589–1592.
Kobayashi et al., 1993, FEBS, 335:171–175.
Lazaro et al., 1996, Neuroscience Letters, 218:21–24.
Lazzaro et al., 1997, Journal of Neurochemistry, 69:348.
Lew et al., 1994, Nature, 371:423–426.
Liu et al., 1995, American Journal of Pathology, 146:228–238.

(Continued)

*Primary Examiner*—Ram R. Shukla
(74) *Attorney, Agent, or Firm*—Jones Day

(57) ABSTRACT

The present invention discloses that DARPP-32 is substrate for the cyclin dependent kinase Cdk5. The phosphorylation takes place at a specific threonine residue of DARPP-32 (Threonine 75). The Cdk5 catalyzed phosphorylation of DARPP-32 converts this protein into an inhibitor of the cAMP dependent protein kinase (PKA) and furthermore prevents it from being converted to an inhibitor of protein phosphatase 1 (PP1). Methods of identifying agents that modulate the phosphorylation of DARPP-32 by Cdk5 are disclosed. Methods of treating dopamine dysfunction in animal subjects are also provided.

2 Claims, 12 Drawing Sheets

OTHER PUBLICATIONS

Meijer et al., 1997, Eur. J. Biochem., 243:527–536.
Miyajima et al., 1995, NeuroReport 6:1130–1132.
Moorthamer et al., 1999, FEBS Letters, 446:343–350.
Nakamura et al., 1997, Neurology, 48:267–270.
Nakamura et al., 1997, Acta Neuropathol, 94:153–157.
Ohshima et al., 1995, Genomics, 28:585–588.
Ohshima et al., 1996, Proc. Natl, Acad. Sci., 93:11173–11178.
Ouimet et al., 1998, Brain Research, 808:8–12.
Pant et al., 1997, Brain Research, 765:259–266.
Pant and Veeranna, 1995, Biochem. Cell Biol., 73:575–592.
Park et al., 1997, The Journal of Neuroscience, 17:8975–8983.
Pato et al., 1996, The Journal of Biological Chemistry, 271:2689–2695.
Pawson and Scott, 1997, Science, 278:2075–2080.
Philpott et al., 1999, Developmental Biology 207:119–132.
Pigino et al., 1997, Journal of Cell Science, 110:257–270.
Roche et al., 1996, Neuron, 16:1179–1188.
Saito et al., 1998, Biochemical and Biophysical Research Communications, 252:775–778.
Sauer et al., 1996, Molecular Biology of the Cell, 7:1759–1769.
Sharma et al., 1999, J. Neurochem., 73:79–86.
Sharma et al., 1999, The Journal of Biological Chemistry, 274:9600–9606.
Sharma et al., 1998, Biochemistry, 37:4759–4766.
Shuang et al., 1998, The Journal of Biological Chemistry, 273:4957–4966.
Snyder et al., 1992, The Journal of Neuroscience, 12:3071–3083.
Songyang et al., 1996, Molecular and Cellular Biology, 16:6486–6493.
Sun et al., 1996, The Journal of Biological Chemistry, 271:14245–14251.
Surmeier et al., 1995, Neuron, 14:385–397.
Takahashi et al., 1995, The Journal of Neuroscience, 15:6222–6229.
Tsai et al., 1993, Development, 119:1029–1040.
Tsai et al., 1994, Nature, 371:419–423.
Tsai et al., 1998, Society for Neuroscience, 24:284 Article No. 116.4.
Veeranna et al., 1997, Dev Neurosci, 19:172–183.
Veeranna et al., 1996, Neurochemical Research, 21:629–636.
Veeranna et al., 1995, J. Neurochem., 64:2681–2690.
Westphal et al., 1999, The Journal of Biological Chemistry, 274:687–692.
Xiong et al., 1997, Molecular and Cellular Biology, 17:6585–6597.
Yamaguchi et al., 1996, Acta Neuropathol, 92:232–241.
Zhang et al., 1997, Developmental Biology 183:222–233.
Bibb et al., 1999, *Nature,* 402:669–71.
Greengard et al., (Jul.) 1999, Beyond the dopamine receptor: the DARPP–32/protein phosphatase–1 cascade, Neuron 23: 435–47.
Hiroi et al., 1999, Neuronal and behavioral abnormalities in striatal function in DARPP–32 mutant mice, European Journal of Neuroscience 11:1114–18.
Masserano et al., 1994, Effects of chronic cocaine administration on $^3$H–dopamine uptake in the nucleus accumbens, striatum and frontal cortex of rats, J. Pharmacol. Exp Ther. 270: 133–41.
Self et al., 1996, Opposite modulation of cocaine–seeking behavior by D1– and D2–like dopamine receptor agonists, Science 271 (5255):1586–89.
Shimosato et al., 1995, Increased polyamine levels and changes in the sensitivity to convulsions during chronic treatment with cocaine in mice, Brain Research 684: 243–47.
Koob and Nestler, 1997, The neurobiology of drug addiction, J. Neuropsychiatry Clin. Neurosci. 9(3):482–97.

* cited by examiner

Potential Therapeutic Targets

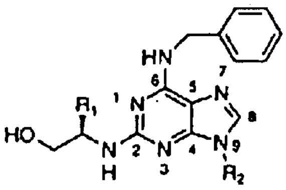
Olomucine: $R_1$= H, $R_2$=Me
(R)-Roscovitine: $R_1$=Et, $R_2$=iPr
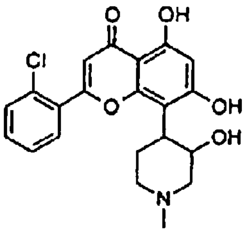
Flavopiridol
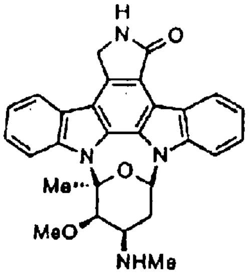
Staurosporine
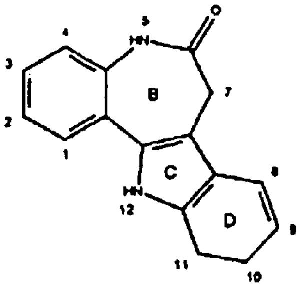
Paullones
Figure 5

*Steps involved in the generation of phosphorylation state-specific antibodies (PSSAb) are illustrated schematically. Typical results of phospho-peptide dot-blot screening of serum are shown. The bottom panel shows immunoblot results confirming the selectivity of the antibody for phosphorylated protein.*

```
          1                                34                 50
Human:    MDPKDRKKIQFSVPAPPSQLDPRQVEMIRRRRPTPAMLPRLSEHSSPEEE
Bovine:   MDPKDRKKIQFSVPAPPSQLDPRQVEMIRRRRPTPAMLFRLSEHSSPEEE
Rat:      MDPKDRKKIQFSVPAPPSQLDPRQVEMIRRRRPTPALLFRVSEHSSPEEE
Mouse:    MDPKDRKKIQFSVPAPPSQLDPRQVEMIRRRRPTPAMLFRVSEHSSPEEE

                                    75                   100
Human:    ASPHQRASGEGHHLKSKRPNPCAYTPPSLKAVQRIAESHLQSISNLNENQ
Bovine:   ASPHQRASGEGHHLKSKRSNPCAYTPPSLKAVQRIAESHLQSISNLGENQ
Rat:      SSPHQRTSGEGHHPKSKRPNPCAYTPPSLKAVQRIAESHLQTISNLSENQ
Mouse:    ASPHQRTSGEGHHPKSKRPNPCAYTPPSLKAVQ-----HLQTISNLSENQ

          102                                137               150
Human:    ASEEEDELGELRELGYPREEDEEEEEEDDEEEEEEEEDSQAEVLKVIRQSAGQK
Bovine:   ASEEEDELGELRELGYPREEEEEEEEEEDEEE--EEDSQAEVLKGSRGSAGQK
Rat:      ASEEEDELGELRELGYPQEDDEEDEDEDEEEDEEEDSQAEVLKGSRGTAGQK
Mouse:    ASEEEDELGELRELGYPQEDDEEDEDEEE--DEEEDSQAEVLKGSRGTVGQK

                                                                200
Human:    TTRGLGLEGPWQRPPPLDESERDGGSEDQVEDPAL-SEPGEEPQRPSPS--E
Bovine:   TTYGQGLEGPWERPPPLDGPQRDGSSEDQVEDPALN-EPGEEPQR--PAHPE
Rat:      LTSGQGLEGPWERPPPLDEPQRDGNSEDQGEGRATQSEPGEEP-RH-PT-PP
Mouse:    PTCGRGLEGPWERPPPLDEPQRDGNSEDQVEGRATLSEPGEEPQ-H-PS-PP

Human:    P-GR   199
Bovine:   P-GT   198
Rat:      ESGT   201
Mouse:           194
```

Figure 7

METHODS OF TREATING DOPAMINE DYSREGULATION USING AGENTS THAT REGULATE PHOSPHORYLATION/ DEPHOSPHORYLATION IN DOPAMINE SIGNALING

CROSS-REFERENCE TO RELATED APPLICATIONS

The present Application is a Continuation-In-Part of U.S. Ser. No. 09/419,379 filed Oct. 15, 1999, now abandoned, the disclosure of which is hereby incorporated by reference in its entirety. The Applicants claim the benefit of this Application under 35 U.S.C. § 120.

GOVERNMENTAL SUPPORT

The research leading to the present invention was supported, at least in part, by a grant from the National Research Service Award Grant No. 5F32 NS10161, National Institute of Mental Health Award Grant No. MH 40899 and the National Institute of Drug Abuse Award Grant No. DA 10044. Accordingly, the Government may have certain rights in the invention.

FIELD OF THE INVENTION

The present invention discloses that DARPP-32 can be phosphorylated at a specific threonine residue by the cyclin dependent kinase 5 (Cdk5). The phosphorylation is shown to significantly alter the properties of DARPP-32. The present invention provides the phosphorylated protein, fragments comprising the phosphorylated threonine residue, and antibodies to the phosphorylated protein. The present invention further provides methods of treating dopamine dysfunction, as well as methods of identifying additional agents which modulate the phosphorylation of DARPP-32 by Cdk5 for such treatments.

BACKGROUND OF THE INVENTION

Dopamine plays an important role as a neurotransmitter in the mammalian nervous system. Indeed, the selective dysregulation of dopaminergic neural transmission has been indicated in a number of neurological disorders including schizophrenia, Parkinson's disease, Huntington's disease, symptoms of attention deficit hyperactivity disorder, Tourette's syndrome, and drug abuse. Virtually all current anti-schizophrenic drugs act as antagonists at a major subclass of dopamine receptors, but are not completely effective and produce undesirable side effects. In addition, cocaine, amphetamines, opiates, nicotine and alcohol have all been shown to be capable of modifying dopaminergic transmission. Therefore, dopaminergic transmission is an important factor in maintaining the mental health of an individual.

A major target for midbrain dopaminergic neurons is the neostriatum. About 95% of all neostriatal neurons have a similar morphology and are referred to as medium-sized spiny neurons. Dopamine- and cyclic AMP (cAMP)-Regulated PhosphoProtein DARPP-32) is a 32 kilodalton cytosolic protein that is selectively enriched in medium-sized spiny neurons in neostriatum [Ouimet et al., *Neurosci* 4:114–124, (1984); Walaas and Greengard, *J Neurosci* 4: 84–98 (1984)]. The sequence of Human DARPP-32 has been determined [Brene et al, *J. Neuroscience,* 14:985–998 (1994); GenBank Accession: AAB30129.1] and a knockout mouse lacking DARPP-32 has been constructed [U.S. Pat. No. 5,777,195, Issued Jul. 7, 1998; Fienberg et al., *Science* 281:838–842 (1998), the contents of each are hereby incorporated by reference herein, in their entireties].

DARPP-32 is phosphorylated by cAMP-dependent protein kinase (PKA) on a single threonine residue, the thirty-fourth amino acid in the sequence, i.e., Thr34 which results in the conversion of DARPP-32 into a potent inhibitor of protein phosphatase-1 (PP1) [Hemmings et al., *Nature* 310: 503–505 (1984)]. DARPP-32 can be dephosphorylated at Thr34 in vitro by the calcium/calmodulin-dependent protein phosphatase, calcineurin [King et al., *J Biol Chem* 259:8080–8083. (1984)]. Dephosphorylation of Thr34 of DARPP-32 removes its inhibitory effect on PP1.

Dopamine has been shown to stimulate the phosphorylation of DARPP-32 in the neostriatum by activation of a biochemical cascade involving stimulation of D1 receptors, activation of adenylyl cyclase, increased cAMP formation and increased activity of PKA [Walaas and Greengard, *J Neurosci* 4:84–98 (1984)]. The selective enrichment of DARPP-32 in dopaminoceptive neurons and its regulation by dopamine strongly indicate that DARPP-32, through regulating protein phosphatase-1 activity, plays a key role in mediating the effects of dopamine on these cells. Indeed, in the brain the chain of events has been described as the DARPP-32/Protein Phosphatase-1 cascade [Greengard et al., *Neuron,* 23:435–447 (1999)].

The control of protein phosphatase-1 activity by DARPP-32 is likely to have a significant role in the regulation of neuronal excitability. For instance, in neostriatum, dopamine-mediated effects on the function of calcium channels [Surmeier et al., *Neuron* 14:385–397 (1995)), voltage-dependent sodium channels [Surmeier et al., *Proc. Nat. Acad. Sci., USA* 89:10178–10182 (1992); Schiffman et al., *Am J Physiol* 483:95–107 (1994)] and $Na^+$,$K^+$-ATPase [Aperia et al., *Proc Natl Acad Sci, USA* 88:2798–2801 (199±1)] are all regulated directly or indirectly by protein phosphatase-1.

Medium-sized spiny neurons of the neostriatum and nucleus accumbens receive dopaminergic input from cell bodies in the midbrain [Anden et al., *Life Science* 3:523–530 (1964); Poirier and Sourkes, *Brain* 88:181–192 (1965); Swanson, *Brain Res Bull* 9: 321–353 (1982)]. To date, five dopamine receptor subtypes have been identified which constitute two major subclasses, a D1 sub family (D1 and D5 subtypes) and a D2 subfamily (D2, D3 and D4 subtypes) [Sibley and Monsma, *Trends in Pharmacol Sci* 13:61–69. (1992)]. D1 and D2 dopamine receptors are abundantly expressed on cell bodies and dendritic processes of medium spiny neurons [Levey et al., *Proc Natl Acad Sci, USA* 90:8861–8865 (1993)]. Messenger RNAs coding for each of the other dopamine receptor subtypes (i.e., D3, D4, a nd D5) have been isolated from individual neostriatal neurons [Surmeier et al., *J Neurosci* 16:6579–91 (1996)], but whether these receptor proteins are expressed in medium spiny neurons and how they functionally interact with D1 and D2 receptors is still unclear.

There is considerable evidence for either synergistic or opposing interactions of D1-like and D2-like dopamine receptors at the biochemical, physiological, and behavioral level [see Jackson and Westlind-Danielsson, *Pharmac Ther* 64:291–370 (1994) for review]. Biochemically, D1 and D2 receptors have opposing actions on the activity of adenylyl cyclase in neostriatal neurons; whereas activation of D1 receptors increases cAMP formation by adenylyl cyclase, D2 receptors inhibit adenylyl cyclase activity [Stoof and Kebabian, Nature 294: 366–368 (1981)]. Studies have shown that D2-like dopamine receptors via interactions with specific G-proteins, can be coupled to multiple effector systems, including calcium channels, potassium channels and phospholipase C [for review, see Huff, *Cell Signal* 8: 453–459 (1996)]. For example, Yan et al. [*Soc. Neurosci. Abst.* 26:1088 (1996)] have shown that D2 receptors on 115 neostriatal neurons negatively couple to calcium channels through a $G_{i/o}$ class protein. In addition, activation of D2 receptors apparently decreases sodium currents in medium spiny neostriatal neurons through a membrane-delimited pathway and increases these currents through a soluble second messenger pathway (presumably involving inhibition of adenylyl cyclase) [Surrneier et al., Proc. Natl. Acad. Sci., USA 89:10178–10182. (1992)].

Heretofore, there has been no particular link between DARPP-32 and Cdk5, a member of the cyclin-dependent kinases (cdks) [See generally, Sherr, Cell 79:551–555 (1994) and Sherr, *Cell* 73:1059–1065 (1993)]. However, Cdk5 [also known as neuronal cyclin-dependent-like protein (Nclk) and tau protein kinase II (TPKII)] has been reported to function in cortical lamination, neurite outgrowth, neuronal plasticity, ischemia, apoptosis, myogenesis and in estrogen signal transduction. This kinase has also been shown to be involved in the hyper-phosphorylation of neurofilaments, which form neurofibulary tangles observed in a number of neurodegenerative diseases.

Cdk5 has been designated a member of the cyclin-dependent kinase family based on its high degree of DNA and amino acid sequence homology with other cdks. However, whereas active cyclin dependent kinases consist of a positive regulatory subunit (the cyclin) and a catalytic subunit (the cyclin dependent kinase) Cdk5 atypically can phosphorylate its substrates without the assistance of a cyclin regulatory subunit. Instead, Cdk5 employs a non-cyclin cofactor called neuronal cyclin-dependent-like kinase 5 associated protein (Nck5 a). There are at least two isoforms of Nck5a in the brain (p35 and p39) which may also exist as proteolytic fragments (i.e., p25 and p29, respectively).

Cyclin dependent kinases play an important role during the cellular replication cycle with the regulation of the human cell cycle requiring the periodic formation, activation, and inactivation of protein kinase complexes that consist of a cyclin subunit and a cdk subunit. Indeed, there has been significant interest in cdks in regard to cancer treatment due to the role of cdks in cell division. In contrast, in adults, Cdk5 is not only most highly expressed in the brain, it is also expressed throughout the brain, and furthermore is only active in the brain. Since brain cells are for the most part post-mitotic, i.e., they no longer divide, Cdk5 also is an atypical member of the cyclin-dependent kinase family because it appears to have a role that is independent of cell division.

Heretofore, most of the drugs that are used to treat dopamine-related disorders function at the extracellular surfaces as either D1 receptor agonists or D2 receptor antagonists. These compounds often have a limited period of efficacy and produce unwanted side-effects. Many of these unwanted side-effects are the result of the lack of specificity of the drug for its target. Therefore, there is a ne ed to provide new drugs assays which can be used to develop novel drugs that can be used to treat dopamine-related disorders. Such novel drugs would have great er specificity than those currently used and therefore, would be less likely to have unwanted side-effects. Furthermore, there is a need to develop treatments for diseases/conditions which are due, at least in part, to an aberration or dysregulation of a pathway effected by the neurotransmission of dopamine.

The citation of any reference herein should not be construed as an admission that such reference is available as "Prior Art" to the instant application.

SUMMARY OF THE INVENTION

The present invention provides a means of exploiting the novel determination that DARPP-32 can be phosphorylated on Threonine-75, and that phospho-Thr75 DARPP-32 is an inhibitor of cAMP-dependent protein kinase (PKA). The present invention further provides new methodology for identifying compounds that modulate this phosphorylation reaction. Such compounds may be used in the treatment of dopamine-related diseases including schizophrenia, Parkinson's disease, Tourette's syndrome, Huntington's disease, attention deficit hyperactivity disorder, and drug abuse. In addition, methods of treating dopamine dysfunction in animal subjects, preferably in humans, are also provided. The present invention further provides compositions that are useful in the identification of the compounds and/or in the treatment of the diseases.

Therefore, the present invention provides an isolated phosphorylated mammalian DARPP-32 protein comprising a phosphorylated threonine residue that can be reversibly phosphorylated and dephosphorylated, and which when that threonine residue is dephosphorylated, it can be re-phosphorylated by cyclin dependent kinase 5 (Cdk5). Preferably the phosphorylated mammalian DARPP-32 protein can inhibit the kinase activity of PKA. In a particular embodiment the phosphorylated mammalian DARPP-32 protein that has the amino acid sequence of SEQ ID NO: 1 and the threonine residue is the seventy-fifth (75) amino acid residue of the amino acid sequence. In a related embodiment the phosphorylated mammalian DARPP-32 protein has the amino acid sequence of SEQ ID NO: 1 having a conservative amino acid substitution, and the threonine residue is the seventy-fifth (75) amino acid residue of the amino acid sequence.

The present invention also provides phosphorylated fragments of a DARPP-32 protein in which the fragments comprise a phosphorylated threonine residue, that when dephosphorylated, can be re-phosphorylated by Cdk5. In a particular embodiment the phosphorylated mammalian DARPP-32 protein fragment is a fragment of a DARPP-32 protein having the amino acid sequence of SEQ ID NO: 1, and the threonine residue is the seventy-fifth (75) amino acid residue of the amino acid sequence of SEQ ID NO: 1. In a related embodiment the phosphorylated mammalian DARPP-32 protein fragment is a fragment of a DARPP-32 protein has the amino acid sequence of SEQ ID NO: 1 having a conservative amino acid substitution, and the threonine residue is the seventy-fifth (75) amino acid residue of the amino acid sequence.

The present invention also provides fusion and/or chimeric peptides and proteins comprising the fragments of phosphoThr75 DARPP-32 protein or the full-length phosphoThr75 DARPP-32 protein.

The present invention further provides phosphorylation state-specific antibodies that have specificity for a phosphorylated mammalian DARPP-32 protein comprising a phosphorylated threonine residue that can be reversibly phosphorylated and dephosphorylated, and which when that threonine residue is dephosphorylated, the threonine can be re-phosphorylated by Cdk5. In a preferred embodiment the Thr75-phosphorylated DARPP-32 has the amino acid sequence of SEQ ID NO: 1. In a related embodiment the Thr75-phosphorylated DARPP-32 has the amino acid sequence of SEQ ID NO:1 having a conservative amino acid substitution. In a particular embodiment the phosphorylation state-specific antibody is a polyclonal antibody. In another embodiment the phosphorylation state-specific antibody is a monoclonal antibody. In still another embodiment the phosphorylation state-specific antibody is a chimeric antibody.

The present invention also provides methods of identifying agents (or drugs) that can modulate the phosphorylation state of Thr75 DARPP-32. Such agents are preferably small organic molecules. One such method comprises contacting a potential agent with Cdk5 and DARPP-32 and determining the amount phosphorylation of DARPP-32. A potential agent is identified as an agent that can modulate the phosphorylation state of Thr75 DARPP-32 if the amount of phosphorylation of DARPP-32 determined is significantly changed in the presence of the potential agent relative to in the absence of the agent. When the amount of phosphorylation is increased the agent is identified as an agonist of Thr75 DARPP-32 phosphorylation, whereas when the amount of phosphorylation is decreased the agent is identified as an antagonist of Thr75 DARPP-32 phosphorylation.

In an alternative embodiment, the rate of phosphorylation of Thr75 DARPP-32 is determined either alone or with the determination of the amount of phosphorylation. In a particular embodiment, an analog of Cdk5 is employed either as the sole kinase or along with Cdk5. In another embodiment the substrate of the analog of Cdk5 is a Cdk5 phosphorylatable fragment of DARPP-32.

The above methods can further comprise contacting the agent with an alternative protein kinase such as a MAP kinase and a substrate for that alternative kinase. The amount (and/or rate) of phosphorylation of the substrate by the alternative kinase is then determined. The alternative kinase preferably is known not to phosphorylate DARPP-32 on Threonine-75. An agent is identified as an agent that can modulate the phosphorylation state of Thr75 DARPP-32 if the amount (and/or rate) of phosphorylation of the substrate for the alternative kinase is not significantly changed in the presence of the agent relative to in the absence of the agent. In a preferred embodiment, the alternative protein kinase is glycogen synthase kinase-3β. More preferably the alternative protein kinase is another cyclin-dependent kinase such as cdk1/cyclin B.

The present invention also provides in vivo methods of identifying agents (or drugs) that can modulate the phosphorylation state of Thr75 DARPP-32. Such methods can be employed alone or in conjunction with in vitro and in situ methods as exemplified herein. One such method comprises administering the agent to a non-human mammal, preferably along with a dopamine D1 receptor agonist. The amount (and/or rate) of phosphorylation of the PKA substrate is then determined. Since the administration of the dopamine D1 receptor agonist in the absence of the agent results in an increase in the phosphorylation state of a PKA substrate an agent is identified as capable of modulating the phosphorylation state of Thr75 DARPP-32 when the amount (and/or rate) of phosphorylation of the substrate is significantly decreased in the presence of the agent relative to in the absence of the agent. In a particular embodiment the PKA substrate is naturally occurring in the non-human mammal. In a preferred embodiments of this type the non-human mammal is a rodent. In a more preferred embodiment of this type the rodent is a mouse.

The in vivo method can further comprise administering the agent to a DARPP-32 knockout non-human mammal, e.g., a homozygous DARPP-32 knockout mouse [see U.S. Pat. No. 5,777,195, Issued Jul. 7, 1998; Fienberg et al., *Science* 281:838–842 (1998)] Preferably the agent is administered along with a dopamine D1 receptor agonist. The amount (and/or rate) of phosphorylation of the PKA substrate is then determined. Since the administration of the dopamine D1 receptor agonist in the absence of the agent results in an increase in the phosphorylation state of a PKA substrate, an agent is identified as capable of modulating the phosphorylation state of Thr75 DARPP-32 when the amount (and/or rate) of phosphorylation of the substrate is not significantly changed in the presence of the agent relative to in the absence of the agent. In a particular embodiment the PKA substrate is naturally occurring in the non-human mammal.

Alternatively, or in conjunction with the above in vivo and/or in situ and/or in vitro methods the locomotor activity of the animal subject, for example, can be determined as described in Example 2 below.

Preferably the agent identified by a method of the present invention can cross and more preferably readily pass through the blood brain barrier. Alternatively, the agent can be modified or otherwise altered so that it can cross or be transported across the blood brain barrier.

As would be clearly understood by a person of ordinary skill in the art, any and/or all of the above embodiments for identifying an agent (or drug) that can modulate the phosphorylation state of Thr75 DARPP-32 including such procedures that incorporate rational drug design, as exemplified below, can be combined to form additional drug screens and assays, all of which are contemplated by the present invention.

In addition, the present invention provides methods for treating dopamine dysregulation in an individual (e.g., a patient) or an animal subject. One such embodiment comprises administering to the individual an agent that inhibits the phosphorylation of Thr75-DARPP-32. In another embodiment the agent promotes the dephosphorylation of Thr75-DARPP-32. In a particular embodiment, the method treats dopamine dysregulation that is related to a symptom and/or disease state characteristic of schizophrenia. In another embodiment the method treats dopamine dysregulation that is related to a symptom and/or disease state characteristic of Parkinson's Disease. In still another embodiment the method treats dopamine dysregulation that is related to a symptom and/or disease state characteristic of Tourette's syndrome. In yet another embodiment the method treats dopamine dysregulation that is related to a symptom and/or disease state characteristic of Huntington's disease. In still another embodiment the method treats dopamine dysregulation that is related to a symptom and/or condition characteristic of drug abuse. In a preferred embodiment the method treats dopamine dysregulation that is related to a symptom and/or condition characteristic of attention deficit hyperactivity. Preferably the agent can cross through the blood brain barrier in sufficient quantities and at a sufficient rate so as to allow the treatment of the dopamine dysregulation and thereby the condition or disease. In one such embodiment the agent is administered intravenously. In another embodiment, the agent is administered orally. More preferably the agent can cross the blood brain carrier without a carrier.

In a particular embodiment, the phosphorylation of Thr75-DARPP-32 is inhibited by inhibiting Cdk5. In a preferred embodiment the agent is roscovitine. In another embodiment, the agent is an indirubin. In a preferred embodiment of this type the agent is indirubin-3'-monoxime. In another embodiment the agent is a paullone. In a preferred embodiment of this type the agent is alsterpaullone.

Accordingly, it is a principal object of the present invention to provide methods of treating diseases and/or conditions that are effected by the DARPP-32/Protein Phosphatase-1 cascade in the brain.

It is a further object of the present invention to provide methods of identifying agents/drugs that can modulate the phosphorylation state of Thr75 DARPP-32.

It is a further object of the present invention to provide compositions such as phosphorylation state-specific antibodies including humanized antibodies for use in treating dopamine-related diseases or conditions.

It is a further object of the present invention to provide kits containing such reagents.

It is a further object of the present invention to provide a method of screening potential drugs in order to select an agent that can potentially ameliorate and/or be used in treatment of Huntington's disease, Parkinson's disease, schizophrenia, Tourette's syndrome, drug abuse, and/or attention deficit disorder.

It is a further object of the present invention to provide a method of administrating an agent, preferably identified by the methods disclosed herein, that can ameliorate a symptom of a dopamine-related disease and/or condition.

These and other aspects of the present invention will be better appreciated by reference to the following drawings and Detailed Description.

BRIEF DESCRIPTION OF THE DRAWINGS

FIGS. 1*a*-1*b* show the phosphorylation of DARPP-32 by striatal Cdk5. Cdk5 was immunoprecipitated, as described [Tsai et al., *Development* 119:1029–1040 (1993)], from 100 $\mu$g of acutely dissected striatal homogenate prepared from wild type (lanes 14) or $p35^{-/-}$ (lane 5) mice. The immunoprecipitated complex from wild type mice contained both Cdk5 and its cofactor p35, as determined by immunoblotting (antibodies from Santa Cruz Biotechnology,). Roscovitine (50 $\mu$M), a selective Cdk5 inhibitor, was included as indicated. The precipitates were used to phosphorylate purified recombinant DARPP-32 at a dilution of 1:20. Reaction mixtures containing 600 $\mu$Ci/ml [$\gamma$-$^{32}$P]ATP were incubated for 0 min (lane 1) or 60 min (lanes 2–5), followed by addition of gel loading buffer (final concentrations, 1% SDS, 12% glycerol, 25 mM DTT), and boiling for 5 min. Samples were subjected to SDS-PAGE (15% acrylamide), gels were dried, and radiographic images were generated using a PhosphorImager (Molecular Dynamics). FIG. 1*c* shows the phosphorylation of DARPP-32 at Thr75 by recombinant Cdk5. Reaction mixtures containing 10 $\mu$M DARPP-32, 200 $\mu$M ATP, 30 mM MOPS (pH 7.2), and 5 mM $MgCl_2$ were incubated for 60 min in the absence or presence of 30 $\mu$g/ml each of partially purified GST-Cdk5 and GST-p25 (active fragment of p35) at 30° C.

Reaction mixtures were processed as above, followed by electrophoretic transfer to nitrocellulose and immunoblotting using a phospho-Thr75 phosphorylation state-specific antibody prepared as described [Czernik et al., in Regulatory Protein Modification (ed., H. C. Hemming, Jr) Pg. 219–246 (Humana, Tototwa N.J. (1997)]. FIGS. 1*d*–1*e* show the phosphorylation of DARPP-32 at Thr75 in intact striatum. Striatal tissue from wild type (lane 1) or $p35^{-/-}$ (lane 2) mice was homogenized by sonication in boiling 1% SDS and 50 mM NaF. Equal amounts of protein were processed as described above and immunoblots were probed with antibodies to phospho-Thr75 DARPP-32 and total DARPP-32.

FIGS. 2*a*-2*c* show the effect of roscovitine on phospho-Thr75 and phospho-Thr34. Mouse striatal slices were prepared and incubated in the absence (Con.) or presence (Ros.) of 10 $\mu$M roscovitine for 1 hour, using standard methodology [Snyder el al., *J. Neurosci.* 12:3071–3083 (1992)]. Tissue was processed as described in the legend to FIGS. 1*a*-1*e* and immunoblotted for phospho-Thr75 (FIG. 2*a*), total DARPP-32 (FIG. 2*b*), or phospho-Thr34 (FIG. 2*c*). FIG. 2*d* shows the phosphorylation by PKA of dephospho-DARPP-32 and phospho-Thr75 DARPP-32. Purified DARPP-32 was phosphorylated to a stoichiometry of 0.93 mol/mol using native cdk1/cyclin B purified from sea star. Phospho-Thr75 DARPP-32 was precipitated from the reaction mixture with 5% TCA, resuspended in 1M Tris-HCl (pH 8.8), and dialyzed against 10 mM HEPES (pH 7.4). Dephospho- and phospho-Thr75 DARPP-32 were phosphorylated by PKA in the presence of [$\gamma$-$^{32}$P]ATP as previously described [Girault et al., *J. Biol. Chem.* 264:21748–21759 (1989)] and subjected to SDS-PAGE. FIG. 2*d* shows the radiographic image of $^{32}$P-labeled DARPP-32; FIG. 2*e* shows the Coomassie brilliant blue stain; and FIG. 2*f* shows the quantitation by PhosphorImager analysis of phosphorylation by PKA of dephospho-DARPP-32 and Phospho-Thr75 DARPP-32. FIG. 2*g* depicts a Lineweaver-Burki kinetic analysis of PKA phosphorylation of ARPP-21 in the presence of 0 (○), 5 (□), 10 (◇), or 15 (Δ) $\mu$M Phospho-Thr75 DARPP-32. Reactions were carried out as described [Hemmings et al., *J. Biol. Chem.* 264:7726–7733 (1989)]. The insert in FIG. 2*g* shows the secondary plot from which the $K_i$ value was derived.

FIGS. 3*a*-3*b* show the effect of roscovitine on phosphorylation of GluR1 and ARPP-16. Striatal slices from either wild type or DARPP-$32^{-/-}$ mice were incubated for 1 h in the absence (Con.) or presence (Ros.) of 10 $\mu$M roscovitine. Homogenates were processed using 10–20% acrylamide gradient gels as described in the legend to FIGS. 2*a*–2*g* and immunoblots were carried out with antibodies to phospho-Ser845 GluR1 or phospho-Ser88 ARPP-16. FIGS. 3*c*-3*f* show the dopamine signaling in wildtype and $p35^{-/-}$ mice. Striatal slices from wildtype and $p35^{-/-}$ mice were incubated for 10 min in the absence (Con.) or presence (D1) of 1 $\mu$M SKF 81297, a selective D1 receptor agonist. Homogenates were processed as above and immunoblotting was carried out with antibodies directed against the PKA phosphorylation sites of the proteins indicated at the left of each panel phospho-Ser845 GluR1, n=4; (phospho-Thr34 DARPP-32, n=6; phospho-Ser55 ARPP-21, n=4; and phospho-Ser88 ARPP-16, n=2; *p<0.05 versus control, †p<0.05 versus wt D1, by ANOVA with Newman-Kuel post-hoc test). FIGS. 3*g* and 3*h* show the effect of roscovitine on whole cell $Ca^{2+}$ current. FIG. 3*g* is a plot of peak $Ca^{2+}$ current versus time in striatal neurons. FIG. 3*h* is a box-plot summary of the roscovitine-induced increase of $Ca^{2+}$ current. Peak voltage-gated $Ca^{2+}$ current in acutely dissociated striatal neurons was recorded from wildtype and DARPP-32' mice in response to bath application of 10 $\mu$M roscovitine (shaded area). Standard whole-cell patch-clamp techniques were used as described [Surmeier et al., Neuron 14:385–397 (1995)].

FIG. 5 (PRIOR ART) displays the chemical structures of olomucine, flavopiridol, staurosporine and Paullone which inhibit Cdk5 kinase activity by competitively binding to the ATP binding site.

FIG. 6A depicts a short synthetic phospho-peptide corresponding to the region surrounding the target site, phospho-Thr75 DARPP-32. FIG. 6B schematically depicts the conjugation of the phospho-peptide to a carrier protein (in this example, *Limulus* Hemocyanin) and the preparation for inoculation of the rabbit. FIG. 6C represents the inoculation, boosting and bleeding of rabbits to obtain the sera containing the desired antibody. Typical results of phospho-peptide immuno-dot-blot screening of serum are shown in FIG. 6D. FIG. 6E represents the purification of the phospho-specific antibody (Ab). The purification used Protein A and phospho/dephosphopeptide affinity chromatography [Czernik et al., in *Regulatory Protein Modification* (ed., H. C. Hemming, Jr) Pg. 219–246 (Humana, Tototwa N.J. (1997)]. FIG. 6F shows immunoblot results confirming the selectivity of the antibody for phosphorylated protein.

FIG. 7 shows the alignment of the amino acid sequences of various DARPP-32 isoforms (bovine, SEQ ID NO:4; rat, SEQ ID NO:3; and mouse, SEQ ID NO:2). The amino acid sequences as shown are deduced from their corresponding cDNA nucleic acid sequences. The alignments include spaces introduced by dashes where necessary. The numbers refer to the position of amino acids relative to the bovine sequence. The total number of amino acids is indicated at the end of each sequence. Nonconserved amino acid differences are shown in bold. Underlined sequences represent synthetic peptides that have been used to generate antibodies, including those that are phosphorylation state-specific. The phospho-peptide used to generate the P-Thr75 DARPP-32 phosphorylation state-specific antibody was CAYTPPSLK (SEQ ID NO:5), where the threonine residue was chemically phosphorylated.

FIG. 8A shows the cDNA expression arrays probed with radiolabeled cDNA from control mice (−ΔFosB) (left) or transgenic mice overexpressing ΔFosB (+ΔFosB) (right). The positions of oligonucleotides encoding ΔFosB and Cdk5 are indicated. FIG. 8B shows the comparison of the levels of Cdk5 gene expression by in situ hybridization. Representative labelings are shown for sections from inducible transgenic mice on (Dox) or off doxycycline ($H_2O$) (left) and rats treated chronically with saline or cocaine (right). Quantitation of signals in the caudatoputaman (CP) and nucleus accumbens (NA) are shown. FIG. 8C shows the comparison of the levels of Cdk5 protein. Representative Cdk5 immunoblots of striatal tissue dissected from inducible transgenic mice on or off doxycycline (left) and from rats treated chronically with saline or cocaine (right) are shown with quantitation. Data represent means ±SEM for n=6; *p<0.05 compared to control, Student's t test.

FIG. 9A shows the locomotor activity for rats, given intra-accumbens infusions of saline or roscovitine and i.p. injections of saline or cocaine, from 50 to 60 min post-injection on successive days 1–5. FIG. 9B shows the behavioral effects of each treatment on day 5 measured for 60 minutes post injection with values plotted at 10 min intervals. FIG. 9C shows the behavioral effects of intra-accumbens infusion of olomoucine (left panel) or the inactive analog, iso-olomoucine on cocaine (i.p.)-induced locomotor activity from 40–50 min post-injection at days 1 and 3 of treatment. All data represent mean activity counts +SEM measured by photocell over test period, *p<0.05, **p<0.001 by ANOVA and post hoc Sheffe's F-test. For day 3 in panel A, p<0.07. For panels A and B, Sal/Sal, n=6; Sal/Coc, n=11; Sal/Coc, n=9; Ros/Coc, n=11. For panel C, Sal/Sal, n=6, Sal/Coc, n=9, Olo/Coc, n=11; Iso/Coc, n=11.

FIG. 10A shows the quantitative immunoblot analysis of level of phospho-Thr75 DARPP-32 in striatal tissue dissected from inducible ΔFosB transgenic mice on or off doxycycline. Representative blots are shown for phospho-Thr75 DARPP-32 and total DARPP-32 in the top two panels and quantitation is shown in the bottom panel. FIGS. 10B and 10C show the level of phospho-Thr75 DARPP-32 in caudatoputamen (FIG. 10B) and nucleus accumbens (FIG. 10C) from rats treated with saline or chronic cocaine administration for 10 days. Data represent means±SEM for n=6; *p=<0.05, Mann Whitney nonparametric t test.

FIG. 11A shows the effect of the selective D, agonist SKF 81297 (D1), in comparison to untreated controls (Con), on PKA phosphorylation of DARPP-32 (left), ARPP-21 (middle), and ARPP-16 (right) in striatal slices from saline and cocaine-treated rats. FIG. 11B shows the effects of chronic cocaine on PKA phosphorylation of DARPP-32 and GluR1 in striatal homogenates. Data in FIGS. 11A and 11B represent means ±SEM, *p<0.01 versus controls, Mann Whitney nonparametric t test, n=6. FIG. 11C shows the effect of chronic cocaine on ligand-gated AMPA current. Kainate-sensitive AMPA current recordings in saline-treated or cocaine-treated rats (left) and statistical analyses (right) are shown. Data represent means ±SEM, *p<0.01 versus controls, unpaired t test, n=6.

DETAILED DESCRIPTION OF THE INVENTION

As disclosed herein, a single protein can, dependent on the particular amino acid residue phosphorylated, function either as a kinase or phosphatase inhibitor. DARPP-32 (Dopamine and cyclic AMP-Regulated Phospho-Protein, $M_r$ 32 kDa) is known to be converted into an inhibitor of protein phosphatase 1 (PP1) when phosphorylated by cAMP dependent protein kinase (PKA) at threonine-34 (Thr34). Indeed, schizophrenia can be treated by inhibiting the dephosphorylation of thr34-phosphorylated DARPP-32 (U.S. Pat. No. 6,013,621, Issued Jan. 11, 2000, the contents of which are hereby incorporated by reference in their entireties.] The present invention shows that DARPP-32 can also be phosphorylated at threonine-75 (Thr75) by cyclin-dependent kinase 5 (Cdk5) and that Cdk5 catalyzed phosphorylation of Thr-75 DARPP-32: (i) prevents DARPP-32 from acting as a substrate for PKA; (ii) converts DARPP-32 into an inhibitor of the PKA, including inhibiting the ability of PKA to phosphorylate other PKA substrates; and (iii) prevents DARPP-32 from being converted to an inhibitor of PP1.

Cdk5 phosphorylates DARPP-32 in vitro and in intact brain cells. Phospho-Thr75 DARPP-32 protein inhibits PKA in vitro by a competitive mechanism. Reduction of phospho-Thr75 DARPP-32 in striatal slices, either by a Cdk5 specific inhibitor or by the use of genetically altered mice, results in increased phosphorylation of PKA substrates and augmented peak voltage-gated $Ca^{2+}$ currents. Thus DARPP-32 is a bifunctional signal transduction molecule which, by distinct mechanisms, controls a major serine/threonine kinase as well as a major serine/threonine phosphatase.

Figure 4A:
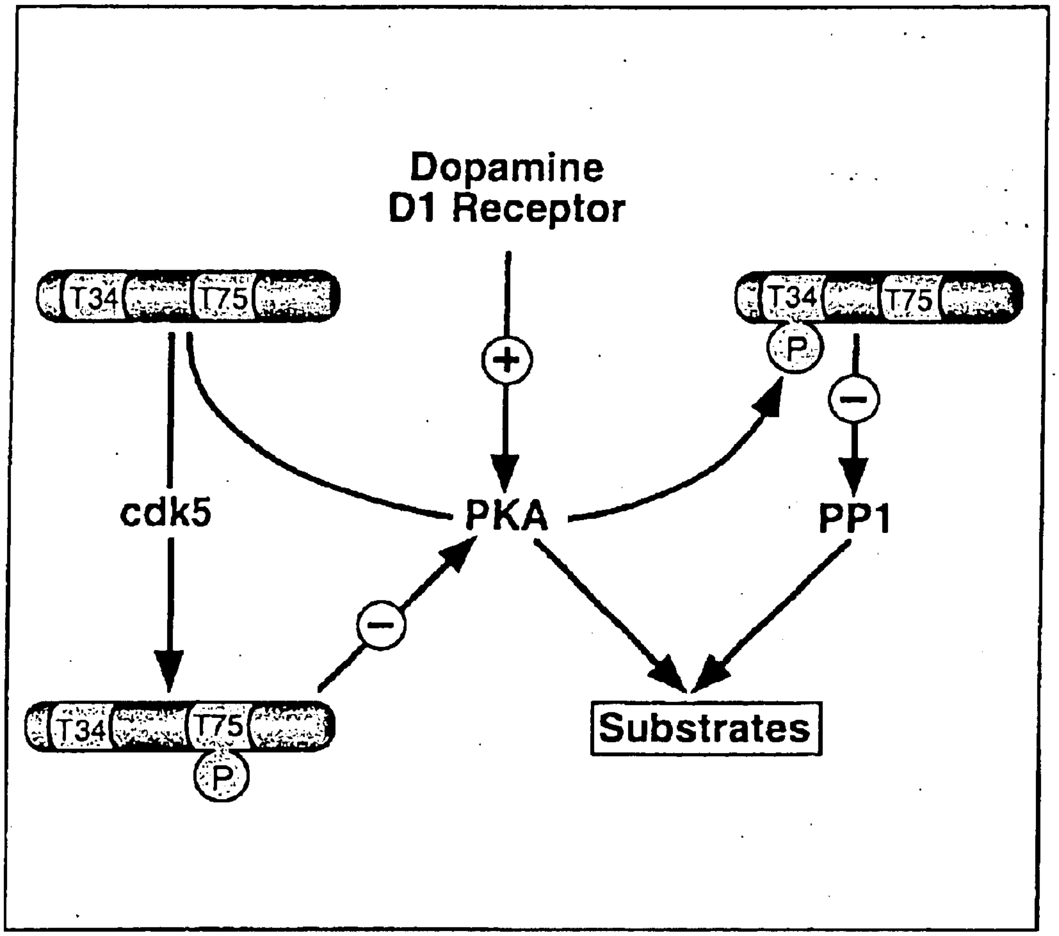
FIG. 4A depicts a model illustrating dual effects of phosphorylation of DARPP-32 in regulation of PKA and PP1 activities. Dopamine D1 receptor activation of PKA and phosphorylation of Thr $^{34}$ by PKA converts DARPP-32 into an inhibitor of PP1. This activation of PKA and inhibition of PP1 contributes synergistically to increased phosphorylation of various substrates including GluR1 AMA receptors, NRA NADA receptors, and calcium channels. Conversely, phosphorylation of DARPP-32 at Thr75 by Cdk5 causes inhibition of PKA and activation of PP1.

In its capacity as a modulator of DARPP-32 phosphoryation, Cdk5 may play a role in Huntington's disease, Parkinson's disease, schizophrenia, Tourette's syndrome, drug abuse, and attention deficit disorder. Indeed, as disclosed herein, Cdk5 plays a key role in DARPP-32 activity, thereby, identifying a whole new set of targets (see FIG. 4*a*), which may serve as the basis for the identification/development of therapeutic agents for dopamine related disorders. Indeed, roscovitine, a specific Cdk5 inhibitor, increases locomotor behavior in rats which is the predicted effect of inhibition of Cdk5 phosphorylation of Thr75 of DARPP-32, thus demonstrating the potential of Cdk5 inhibitors to modulate dopamine dysregulation.

Furthermore, Example 2 below discloses a homeostatic response mechanism to chronic cocaine exposure in which ΔFosB-mediated changes in gene expression are coupled to the regulation of Cdk5 and dopamine signaling in striatal neurons. Thus, Cdk5 is shown to be a downstream target gene of the transcription factor ΔFosB, which accumulates in dopaminoceptive neurons of the striatum with chronic exposure to cocaine. Therefore, as described in Example 2 below, ΔFosB overexpression, and/or chronic cocaine administration raises Cdk5 mRNA, Cdk5 protein levels, and Cdk5 activity in the striatum in mice. Moreover, intra-striatal injection of Cdk5 inhibitors potentiated behavioral effects of repeated cocaine administration. These results demonstrate that ΔFosB-mediated changes in Cdk5 levels and resulting alterations in $D_1$ dopaminergic signaling contribute to adaptive changes in the brain related to cocaine addiction.

Therefore, the present invention provides DARPP-32 that has been phosphorylated at threonine-75 as well as fragments of DARPP-32 comprising phospho-Thr75 DARPP-32. The present invention further provides methods of treating dopamine dysfunction in animals, preferably in humans, by administering to the animal an agent that either inhibits the phosphorylation of Thr75-DARPP-32 or promotes the dephosphorylation of Thr75-DARPP-32. Preferably, the agent can cross, and more preferably readily pass through, the blood brain barrier.

The present invention further provides methods of identifying therapeutic agents that are designed to be more specific and thereby less likely to produce deleterious side-effects. Indeed, any compound that is identified as modulating the level of phosphorylation of threonine-75 of DARPP-32 or modulating the functional activity of DARPP-32 that is phosphorylated on threonine-75 is a potential drug for treating dopamine-related disorders. Thus, the present invention provides methods of identifying potential regulators of Cdk5 kinase activity.

The present invention further provides new methodology for identifying compounds that modulate phospho-Thr75 DARPP-32 concentrations that can be used in the treatment of dopamine-related diseases. Therefore, the present invention also provides DARPP-32 that has been phosphorylated at threonine-75, which may be used as a standard in such drug assays or as an inhibitor of PKA either in vitro and/or in vivo. Similarly, peptide fragments of phosphoThr75 DARPP-32 which contain the phosphorylated Thr75 may also serve as standards in such drug assays or as competitive inhibitors of the Cdk5 catalyzed phosphorylation of DARPP-32 are also provided.

Therefore, if appearing herein, the following terms shall have the definitions set out below.

As used herein the term "DARPP-32" is used interchangeably with "Dopamine- and cyclic AMP (cAMP)-Regulated PhosphoProtein" and is a 32 kilodalton cytosolic protein that is selectively enriched in medium-sized spiny neurons in neostriatum. The human DARPP-32 has the amino acid sequence is SEQ ID NO: 1; the mouse DARPP-32 has the amino acid sequence is SEQ ID NO:2; the rat DARPP-32 has the amino acid sequence is SEQ ID NO:3; and the bovine DARPP-32 has the amino acid sequence is SEQ ID NO:4. The alignment of the latter three sequences are shown in FIG. 7.

As used herein the term "Thr75 DARPP-32" is used interchangeably with "thr$^{75}$DARPP-32", "Threonine-75 DARPP-32" and "threonine-75 DARPP-32" along with analogous abbreviations, and denotes the seventy-fifth amino acid residue in the amino sequence of DARPP-32 as disclosed by Brene et al. [*J. Neurosci.* 14:985–998 (1994)] having the GenBank Accession of AAB30129.1 (SEQ ID NO: 1) which is a threonine residue that, as disclosed herein, can be phosphorylated by Cdk5.

As used herein the term "phospho-Thr75 DARPP-32" or denotes the phosphorylated form of Thr75 DARPP-32.

As used herein the term "Thr34 DARPP-32" is used interchangeably with "thr$^{75}$ DARPP-32" "Threonine-34 DARPP-32" and "threonine-34 DARPP-32" along with analogous abbreviations and denotes the thirty-fourth amino acid residue of the amino sequence of DARPP-32 as disclosed by Brene et al. [*J. Neurosci.* 14:985–998 (1994)] having the GenBank Accession of AAB30129.1 (SEQ ID NO: 1) which is a threonine residue that can be phosphorylated by the cyclic AMP dependent protein kinase (PKA).

As used herein "CDK5", "Cdk5" or "cdk5" are used interchangeably with "cyclin-dependent kinase 5" which is also known as neuronal cyclin-dependent-like protein (Nclk) and tau protein kinase II (TPKII). Cdk5 is a member of the cyclin-dependent kinases but atypically Cdk5 employs a non-cyclin cofactor called neuronal cyclin-dependent-like kinase 5 associated protein (Nck5a) rather than a cyclin. When the term "Cdk5" is used in descriptions of kinase reactions it should be understood that the active form, i.e., the "Cdk5/Nck5a complex" (see below) may be the actual catalytic factor and/or a fragment of Cdk5 which retains at least 10% of the catalytic activity of Cdk5.

As used herein "an analog of Cdk5" is used interchangeably "a homolog of Cdk5" and is a protein kinase that like Cdk5 phosphorylates DARPP-32 on Threonine-75 but not on Threonine-34. One such analog is cdk1.

As used herein "Nck5a" is used interchangeably with "neuronal cyclin-dependent-like kinase 5 associated protein" and is a non-cyclin cofactor for Cdk5. There are at least two isoforms of Nck5a in the brain (p35 and p39) which may also exist as proteolytic fragments (i.e., p25 and p29, respectively).

As used herein the term "Cdk5/Nck5a complex" denotes the complex formed between Cdk5 and Nck5a which is an active form of the Cdk5 kinase.

As used herein the term "Cdk5 phosphorylatable fragment of DARPP-32" is a protein fragment of DARPP-32 that contains a threonine residue that when in the dephosphorylated form can be phosphorylated by Cdk5. For human DARPP-32 having the amino acid sequence of SEQ ID NO: 1, the threonine residue is preferably Thr75 DARPP-32. Such fragments can be between about 5 to 100 residues, or more preferably between about 10 and 50 residues. For example, in a particular embodiment the peptide fragment comprises 5 consecutive amino acids from SEQ ID NO: 1 including Thr75. In another embodiment of this type, the peptide fragment comprises 7 consecutive amino acids from SEQ ID NO: 1 including Thr75. In an alternative embodiment the peptide fragment comprises between 10 to 25 consecutive amino acids from SEQ ID NO: 1 including Thr75. All of the peptide fragments can be part of fusion peptides or proteins. A Cdk5 phosphorylatable fragment of DARPP-32 can be prepared by phosphorylating the dephosphorylated fragment or by cleaving (such as with a protease) the phosphorylated fragment from a larger fragment of phospho-Thr75 DARPP-32 protein or from the full-length phospho-Thr75 DARPP-32 protein. Thus the fragments can be synthesized by either standard peptide synthesis described below, or generated through recombinant DNA technology or by classical proteolysis.

As used herein the amount and/or rate of phosphorylation of DARPP-32 or the Cdk5 phosphorylatable fragment of DARPP-32 in a kinase reaction is "significantly changed" when the amount and/or rate of phosphorylation of DARPP-32 or the Cdk5 phosphorylatable fragment of DARPP-32 is increased or decreased by at least about 10–25%, relative to the control reaction. Preferably, a significant change in rate of the phosphorylation of DARPP-32 by Cdk5 for example, observed in the presence of a potential modulator is at some point correlated with the Michaelis constants (e.g., the Vmax or Km) of the reaction. For example, in the case of an inhibitor a KI can be determined. Thus it may be necessary to study various concentrations of a modulator in a reaction mixture to allow the identification of the potential modulator as a modulator.

As used herein the term "dopamine dysregulation" is used interchangeably with the term "dopamine-related disorder" and specifically includes "dopamine-related diseases". A dopamine-related disorder can be a disease (e.g., Parkinson's disease) or a condition (e.g., addiction to cocaine) that involves an aberration or dysregulation of a pathway effected by dopaminergic neurotransmission in the brain. Preferably the pathway effected includes the phosphorylation and/or dephosphorylation of DARPP-32, with the corresponding treatment of the dysregulation involving the stimulation and/or inhibition of the phosphorylation and/or dephosphorylation of one or more specific threonine residues of DARPP-32. Dopamine-related disorders include schizophrenia, Parkinson's disease, Huntington's disease, symptoms of attention deficit hyperactivity disorder, Tourette's syndrome, and drug abuse [see e.g., Greengard et al., Neuron, 23:435–447 (1999), and Bibb et al., Proc. Nat'l Acad. Sci. 97:6809–6814 (2000) the contents of which are hereby incorporated by reference in their entireties].

As used herein the term "heterologous nucleotide sequence" is a nucleotide sequence that is added to a nucleotide sequence of the present invention by recombinant molecular biological methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like. Thus, the nucleic acids that encode the proteins being used and/or detected in the present invention can comprise a heterologous nucleotide sequence.

As used herein a "small organic molecule" is an organic compound [or organic compound complexed with an inorganic compound (e.g., metal)] that has a molecular weight of less than 3 kilodaltons preferably less than 1.5 kilodaltons.

As used herein the term "about" means within 10 to 15%, preferably within 5 to 10%. For example an amino acid sequence that contains about 60 amino acid residues can contain between 51 to 69 amino acid residues, more preferably 57 to 63 amino acid residues.

Drug Screening

Figure 4B:
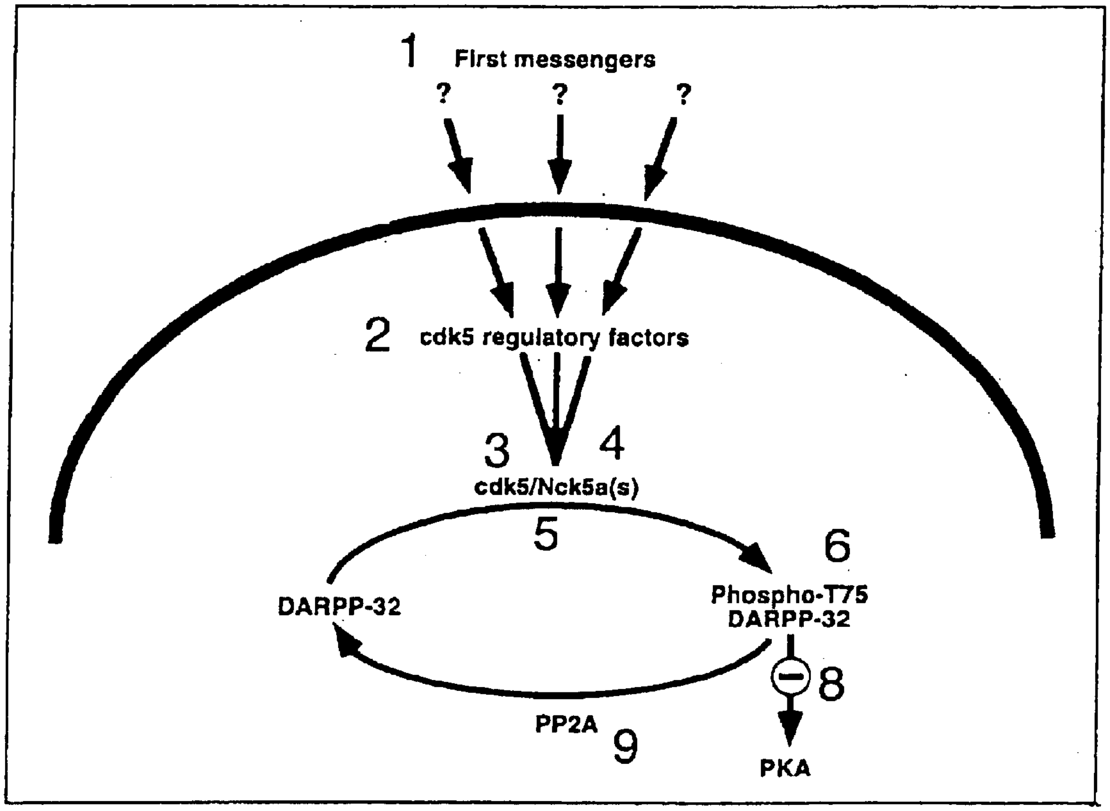
FIG. 4B displays potential therapeutic targets to modulate the phosphorylation state of Threonine-75 (Thr75) of DARPP-32. Modulators of first messengers, neurotransmitters or signal transduction steps upstream of Cdk5 are at one end of the spectrum. Such modulators are anticipated to effect Cdk5 regulatory factors, which in turn, can effect the Cdk5/Nck5a catalyzed phosphorylation of DARPP-32 at Thr75. Phosphorylation of DARPP-32 at Thr75 by Cdk5 causes inhibition of PKA, while dephosphorylation is catalyzed by PP2A.
Figure 6:
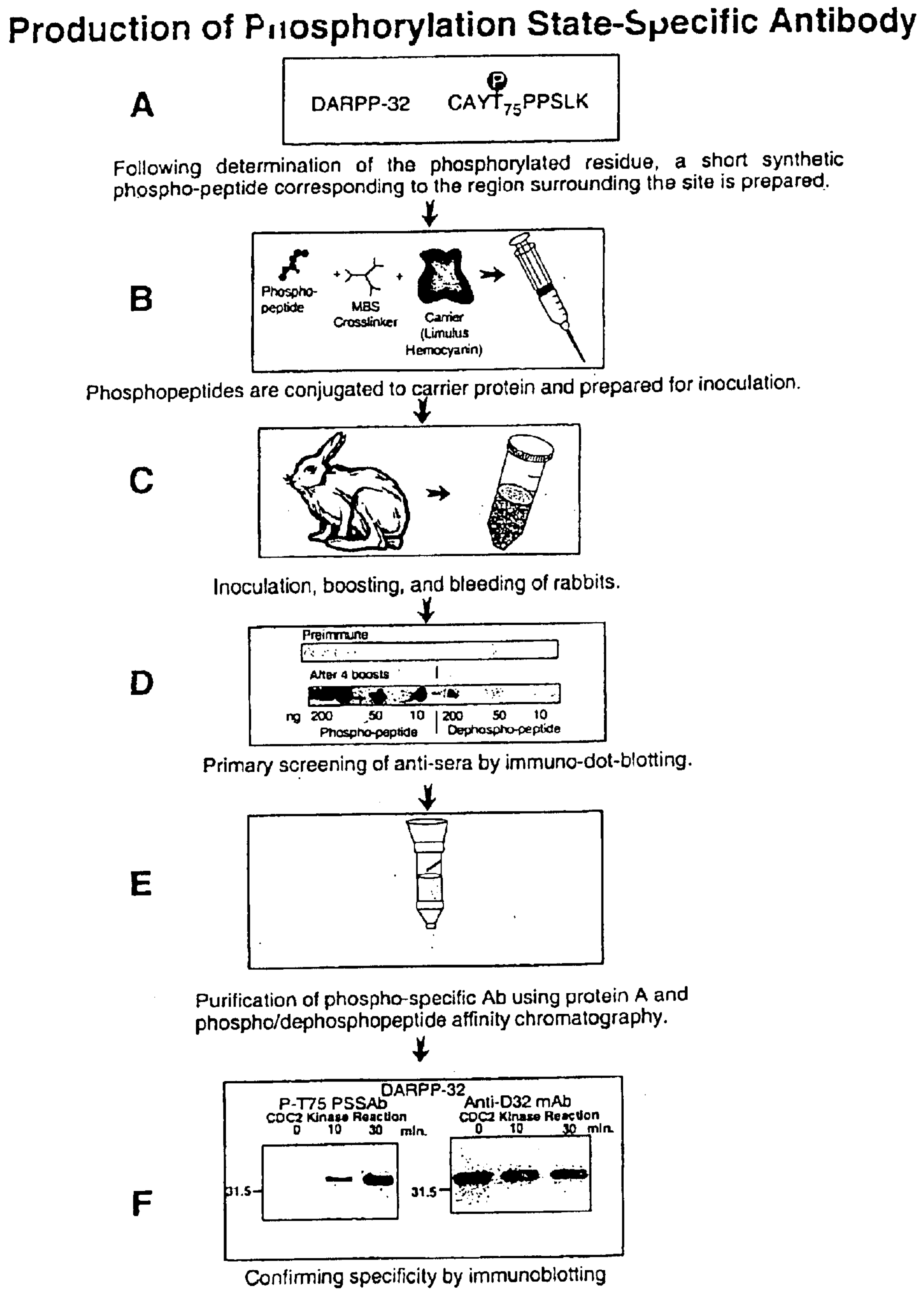
FIGS. 6A–6F schematically show the steps involved in the generation of phosphorylation state-specific antibodies (PSSAb) to Thr71 DARPP-32.

The present invention provides a number of viable targets for screening drugs that can modulate Thr75 DARPP-32 phosphorylation and thereby ameliorate dopamine-related disorders. Potential modulators include small organic molecules that mimic the function of first messengers, and/or analogs thereof, inhibitors, and/or toxins that modulate the processes that effect the phosphorylation of Thr75 DARPP-32 such as represented schematically in FIG. 4B.

One particular target for regulating Thr75 DARPP-32 phosphorylation is Cdk5. Thus, in one drug screen of the present invention compounds are identified that effect the phosphorylation of DARP-32 by Cdk5. In one such embodiment, Cdk5 is added to the reactions that include a drug candidate, ATP, buffering reagents, and an appropriate substrate (e.g., DARPP-32 or a fragment of DARPP-32 encompassing Thr75). In a particular embodiment, one or more kinases that do not phosphorylate Thr75 DARPP-32, such as MAP kinase (see below) are also employed (preferably purified and demonstrated to have in vitro activity) as controls. These kinases can then be added to analogous reactions that include the drug candidate, ATP, buffering reagents, and an appropriate kinase substrate. Combinatorial libraries of chemical compounds, based on different structural skeletons (e.g., purines) as well as unrelated naturally occurring compounds can then be tested as drug candidates. In a preferred embodiment of this type, the assay is performed using high throughput technology with automated robotic technology. Positive results (or a "hit") represent either the reduced or increased phosphorylation of the kinase substrate by Cdk5, as compared to the control reactions (in which the drug candidate is not included in the assay). Preferably the drug candidate has minimal to no effect on the phosphorylation level of the control kinase reactions examined.

Once a drug candidate is selected, structural variants of the drug candidate can be tested. These compounds can also be scrutinized and modified with parameters such as membrane permeability, specificity of effects, and toxicity. The selected inhibitors (e.g., the most potent) of this secondary screening can then be evaluated in situ and in animal models to determine if they alter phospho-Thr75 DARPP-32 concentrations and/or induce the predicted behavior alterations with minimal to no side-effects. Such behavioral abnormalities include testing locomotor activity, e.g., administration of drugs of abuse to mice result in increased locomotor activity [see, Kosten et al., *J. Pharmacol., Exp. Ther.* 269:137–144 (1994) and Example 2 below; and/or self-administration of selected drugs or in prepulse inhibition see generally U.S. Pat. No. 5,777,195 Issued Jul. 7, 1998 hereby incorporated by reference in its entirety]. These tests can be then be followed by human trials in clinical studies. Alternatively, in certain instances, human trials in clinical studies can be performed without animal testing. Compounds affecting targets other than Cdk5 can also be similarly screened, using alternative targets exemplified below.

Alternatively, modulators of Thr75 DARPP-32 phosphorylation including inhibitors of Cdk5 (for example) can be obtained by screening a random peptide library produced by recombinant bacteriophage for example, [Scott and Smith, Science, 249:386–390 (1990); Cwirla et al., *Proc. Natl. Acad. Sci.,* 87:6378–6382 (1990); Devlin et al., *Science,* 249:404–406 (1990)] or a chemical library. Using the "phage method" very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume* 5, Abstract FR:013 (1988); Furka, Int. J. Peptide Protein Res. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as modulators of Thr75 DARPP-32 phosphorylation.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Larn et al., International Patent Publication No. WO 92/00252; Kocis et al., International Patent Publication No. WO 9428028, each of which is incorporated herein by reference in its entirety], and the like can be used to screen for modulators of Thr75 DARPP-32 phosphorylation such as an inhibitor of Cdk5, for example, according to the present invention. Once a potential modulator is identified, chemical analogues can be either selected from a library of chemicals as are commercially available from most large chemical companies including Merck, GlaxoWelcome, Bristol Meyers Squib, MonsantolSearle, Eli Lilly, Novartis and Pharmacia UpJohn, or alternatively synthesized de novo. The prospective agent (drug) can be placed into any standard assay to test its effect on the phosphorylation of Thr75 of DARPP-32 by Cdk5 for example. A drug is then selected that modulates the phosphorylation state of Thr75 of DARPP-32.

The present invention also contemplates screens for small molecules, analogs thereof, as well as screens for natural modulators of Thr75 DARPP-32 phosphorylation such as those that bind to and inhibit Cdk5 in viva. Thus, an analog of roscovitine, which is known to competitively inhibit the binding of ATP to the ATP binding domain in the catalytic site of Cdk5, can be tested in order to obtain a modulator having a more specific and/or potent effect than roscovitine. Alternatively, natural products libraries can be screened using assays of the invention for molecules that antagonize Cdk5 activity. Other families of drugs that have been shown to inhibit Cdk5 include paullones [Lost et al., *Eur. J. Biochem.* 267:5983–5994 (2000) the contents of which are hereby incorporated by reference in their entireties] and indirubins [Leclerc et al., *J. Biol. Chem.* (epub ahead of print Sep. 29, 2000) the contents of which are hereby incorporated by reference in their entireties].

In one particular assay the target e.g., Cdk5 can be attached to a solid support. Methods for placing Cdk5 on the solid support are well known in the art and include such things as linking biotin to Cdk5 and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to Cdk5 can be determined. Alternatively, or in addition, the dissociation constant between the labeled potential modulator and Cdk5, for example can be determined. Suitable labels for either Cdk5 or the potential modulator are exemplified herein. In a particular embodiment, isothermal calorimetry can be used to determine the stability of the Cdk5-Nck5a complex in the absence and presence of the potential modulator.

In another embodiment, a Biacore machine can be used to determine the binding constant of the Cdk5-Nck5a complex in the presence and absence of the potential modulator. Alternatively, Cdk5 can be immobilized on a sensor chip. Nck5a can then be contacted with (e.g., flowed over) the sensor chip to form the Cdk5-Nck5a complex. In this case the dissociation constant for the Cdk5-Nck5a complex can be determined by monitoring changes in the refractive index with respect to time as buffer is passed over the chip. [O'Shannessy et al. Anal. Biochem. 212:457–468 (1993); Schuster et al., *Nature* 365:343–347 (1993)]. Scatchard Plots, for example, can be used in the analysis of the response functions using different concentrations of Nck5a. Flowing a potential modulator at various concentrations over the Cdk5-Nck5a complex and monitoring the response function (e.g., the change in the refractive index with respect to time) allows the dissociation constant for the Cdk5-Nck5a complex to be determined in the presence of the potential modulator and thereby indicates whether the potential modulator is either a stabilizer, or destabilizer of the Cdk5-Nck5a complex.

In another aspect of the present invention a potential modulator can be assayed for its ability to modulate the phosphorylation of Thr75 DARPP-32 or a fragment of DARPP-32 comprising Threonine-75 by Cdk5 (i.e., the Cdk5-Nck5a complex) either independently, or subsequent to a binding assay as exemplified above. In one such embodiment, the amount and/or rate of the phosphorylation is determined of Thr75 DARP-32 or a fragment of DARPP-32 comprising the threonine-75 residue. For such assays labeled [$\gamma$-$^{32}$P]ATP can be used. In a particular embodiment a phosphorylation state specific antibody for Thr75 DARPP-32 can be employed. The determination can include a real-time determination, or alternatively, aliquots from the incubation mixture can be withdrawn at defined intervals and the aliquots can be subsequently placed on nitrocellulose paper or on gels. In a particular embodiment the potential modulator is selected when it is an inhibitor of the phosphorylation reaction.

In an assay in which the Thr75 DARPP-32 phosphorylation is being measured indirectly, e.g., for an effect of the phospho-Thr75 DARPP-32 protein, a control in which the recombinant protein containing a Thr75Ala mutation of DARP-32 can be used to confirm that the phosphorylation of Thr75 DARPP-32 is involved in the effect.

Figure 3:
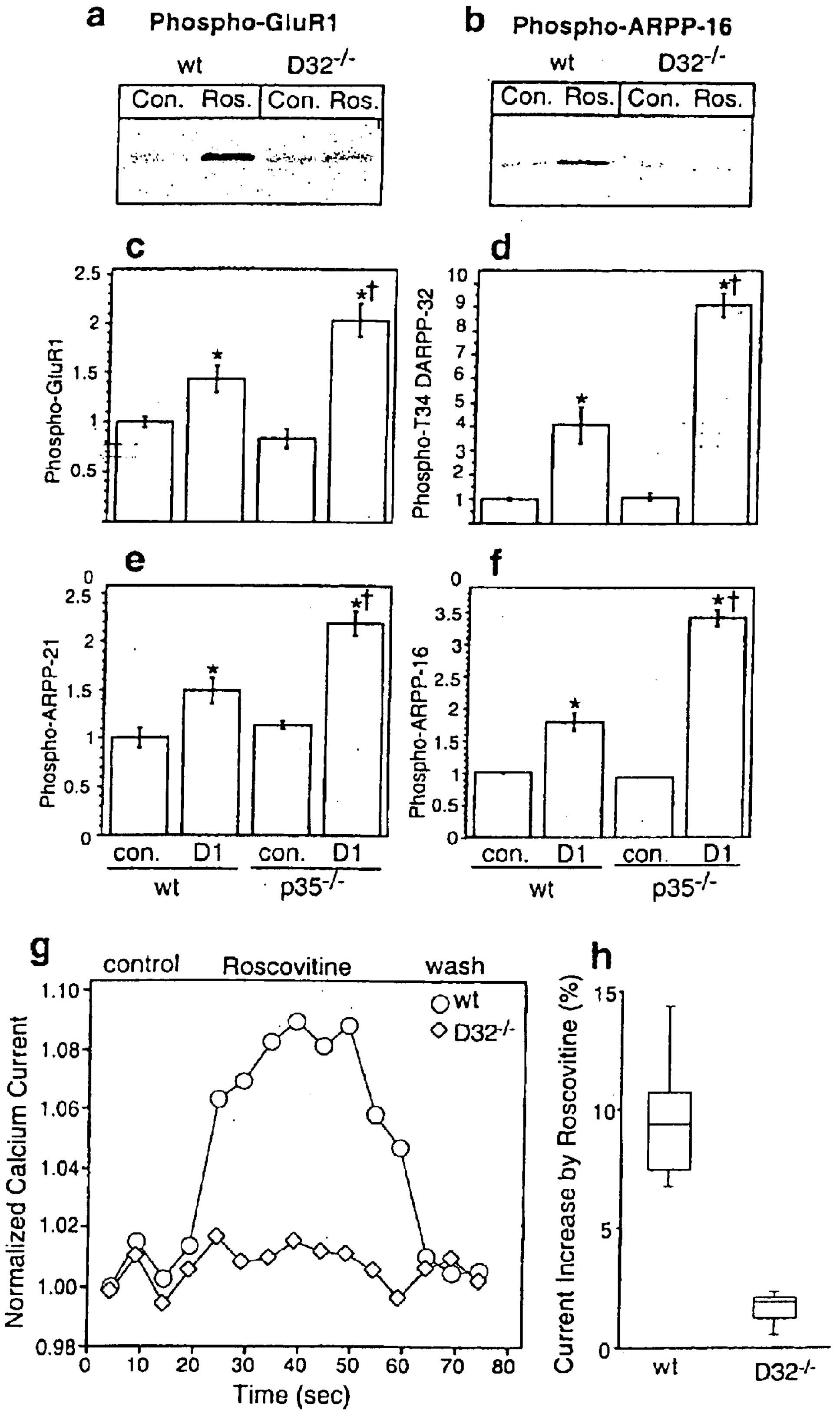
FIGS. 3*a*-3*h* show the effect of reducing phospho-Thr75 DARPP-32 on PKA activity in intact neurons.

Thus, a modulator that inhibits, or in the alternative stimulates the phosphorylation is then selected. In a particular embodiment, the effect of a potential modulator on the catalytic activity is determined. The potential modulator can then be tested for its effect on the physiological consequence of PKA inhibition by phospho-Thr75 DARPP-32. For this purpose, voltage-gated $Ca^{2+}$ currents, (which are known to be regulated by PKA) can be analyzed using patch-clamp recordings of dissociated striatal neurons (see e.g., FIGS. 3*g* and 3*h*) in the presence and absence of the potential modulator of Thr75 DARPP-32 phosphorylation. The whole-cell $Ca^{2+}$ current in the neuron can then be determined. When an increase in the $Ca^{2+}$ current is determined in the presence of the potential modulator relative to in its absence, the potential modulator is selected/identified as an inhibitor of Thr75 DARPP-32 phosphorylation, whereas when a decrease in the $Ca^{2+}$ current is determined in the presence of the potential modulator relative to in its absence, the potential modulator is selected/identified as an agonist of Thr75 DARPP-32 phosphorylation. Such assays can further include testing the potential modulator with striatal neurons from DARPP-32 knockout mice, in which a potential modulator is selected when it shows no effect of the PKA dependent voltage-gated $Ca^{2+}$ currents. Similarly, $P35^{-/-}$ mouse striatal neurons can be employed to ascertain the role of Cdk5 in the effect (as described in Example 1, below).

Alternatively, or in conjunction with the above assays, a potential modulator can be added to striatal tissue slice (as exemplified below). Tissue samples can be treated with various concentrations of a potential modulator and the sample can then be analyzed for DARPP-32 phosphorylation of either threonine-75 or threonine-34. Potential modulators that have the potential to affect phospho-Thr75 (e.g., by affecting one of the processes indicated in FIG. 4B), can be tested for example, on intact neurons in situ by treatment of acutely prepared neostriatal slices incubated in Kreb's bicarbonate buffer solution containing the reagent. The effects of these compounds can be tested by empirically defining the optimal concentration and time of incubation.

Similarly, alternatively, or in conjunction with the above assays an animal model can be used to ascertain the effect of a potential agent on a dopamine related condition. A potential modulator that ameliorates the dopamine related condition can then be selected [see U.S. Pat. No. 5,777,195, Issued Jul. 7, 1998; Fienberg et al., *Science* 281:838–842 (1998), the contents of each are hereby incorporated by reference herein, in their entireties]. For example, locomotor behavioral response of the animal can be determined in the presence and absence of the agent. Since, the phosphorylation of Thr75 DARPP-32 (i) prevents DARPP-32 from acting as a substrate for PKA; (ii) converts DARPP-32 into an inhibitor of the PKA, including inhibiting the ability of PKA to phosphorylate other PKA substrates; and (iii) prevents DARPP-32 from being converted to an inhibitor of PP1, the phosphorylation of Thr75 DARPP-32 can be assumed to potentiate an effect that is opposed to that of the well characterized phospho-Thr34 DARPP-32.

Methods of testing a potential therapeutic agent (e.g., a candidate drug, potential modulator, etc.) in an animal model are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined. Animals can be sacrificed by focused microwave beam irradiation, for example. Striatal tissue can then be dissected and homogenates can be subjected to immunoblot analysis. An alternative approach that can be employed assesses the potential efficacy of these compounds in relieving dopamine related pathological symptoms in animal models for disease. For example, treatment of rats or mice with 6-hyroxydopamine results in loss of dopaminergic afferent neurons, administration of quinolinic acid causes lesion of intrinsic striatal neurons, and MPTP destroys dopamine containing nerve terminals. All of these cause movement disorders and serve as animal models for disorders in dopaminergic neurotransmission. Transgenic animals ectopically expressing the human disease causing form of the Huntington's disease (HD) gene exhibit neuropathalogical symptoms similar to those of HD patients. Models such as these can be used to assess the efficacy of any potential therapeutic agents. Generally, at least two groups of animals are used in the assay, with at least one group being a control group which is administered the administration vehicle without the potential modulator.

There are also a number of potential regulators of Cdk5 activity that can be used as templates for designing potential drug analogs, or alternatively as potential targets for drug assays. Both the ribosomal complex protein, L34, and the DNA binding protein, dbPA have previously been shown to bind and inhibit Cdk5. The neuronal secretory vesicle protein nsec (p67, Munc 18) has also been reported to activate Cdk5. Cdk T14 kinase as well as other kinases including casein kinase I have been implicated in the phosphorylation and regulation of Cdk5 [Sharma et al., *Proc. Natl. Acad. Sci., USA* 96:11156–11160 (1999)]. In addition, p35 has been implicated as a modulator of Cdk5. Interestingly, p35 may be inhibitory whereas, a proteolytically processed fragment of p35 may be activating. In any case, the concentration of p35 in a cell may be the primary mode for regulating Cdk5 activity. Since p35 levels may be regulated through phosphatase-dependent activation of proteosomes, stimulating or inhibiting phosphatase-dependent activation of proteosomes in the striatum could potentially alter the phospho-Thr75 DARPP-32 levels and thereby ameliorate dopamine related disorders. Therefore, such factors can be envisioned as potential targets for the drug assays and screens presented herein.

As disclosed herein, when DARPP-32 is phosphorylated at Thr75 it cannot be phosphorylated by PKA. This phosphorylation of DARPP-32 at Thr-75 could alter its biochemical characteristics so that it can bind PKA, possibly near the active site, in a manner and with adequate affinity such that the PKA substrate site, Thr34 of DARP-32, cannot come into proximity with the catalytic site of PKA. As a result of this phosphorylation-dependent interaction, not only is PKA unable to phosphorylate DARPP-32 but the activity of PKA toward other substrates may be inhibited in a competitive manner. Deletion mutants of DARPP-32 can be generated to define the inhibitor domain. Small phosphopeptides encompassing the Thr75 site may bind to PKA competitively (displacing holophospho-Thr75 DARPP-32) but may have no effect on PKA activity. These peptides could thus serve as the basis for the design of compounds which have the ability to interrupt the PKA inhibitory actions of phospho-Thr75 DARPP-32 in vivo.

In addition, as stated above, DARPP-32 is converted into an inhibitor of PP1 by phosphorylation at Thr34. DARPP-32 is also phosphorylated at Ser102 by casein kinase II (CKII) and at Ser 137 by casein kinase I (CKI). Phosphorylation at Ser102 improves the efficiency of phosphorylation of Thr34 by PKA. Phosphorylation of DARPP-32 at Ser137 reduces the efficiency of dephosphorylation of phospho-Thr34 by protein phosphatase 2B. Thus the net effects of phosphorylation of DARPP-32 at Ser102 and Ser137 by CKI and CKII, respectively, is to enhance the amount of time that DARPP-32 remains in its phospho-Thr34, or PP1 inhibitory state. The effect of phosphorylation of DARPP-32 at Thr75 upon phosphorylation kinetics at these other sites was therefore assessed. While phosphorylation of DARPP-32 by CKI and CKII was unaffected, the effect on PKA phosphorylation was quite dramatic. Thus when DARPP-32 is phosphorylated at Thr75 it may affect the dephosphorylation at any or all of the other 3 phosphorylation sites. DARPP-32 may also serve additional unknown functions and/or serve as a substrate for additional kinases. Phospho-T75 could exert affects on these events and/or functions. Finally, in addition to Thr34 of DARPP-32 serving as a substrate site for PKA it also serves as a substrate site for the cGMP-dependent protein kinase (PKG), which is part of a separate signaling pathway which mediates the effect of nitric oxide in the basal ganglia. Thus phosphorylation of DARPP-32 at Thr75 could affect the ability of DARPP-32 to serve as a substrate for PKG.

Activation of D1 dopamine receptors also appears to reduce phospho-T75 DARPP-32 levels. Phospho-Thr75 DARPP-32 is also dephosphorylated by protein phosphatase 2A (PP2A). PP2A dephosphorylation of Phospho-Thr75 DARPP-32 is itself regulated by PKA phosphorylation of a regulatory subunit of the PP2A phosphatase complex. (Known inhibitors PP2A include okadaic acid and calyculin A). PKA treatment of purified holo-PP2A appears to enhance PP2A dephosphorylation of phospho-T75 DARPP-32. Therefore, PP2A and more specifically the regulatory subunit of the PP2A are particular targets of the present invention for regulating the phosphorylation of Thr75 DARPP-32. In addition, other phosphatases such as PP4, may also dephosphorylate phospho-Thr75 DARPP-32 and therefore may serve as potential drug screen targets. Furthermore, phospho-Thr75 DARPP-32, as disclosed herein, is an inhibitor of PKA. Thus any compound identified that affects these interactions may also serve as the basis of a therapeutic treatment for dopamine-related diseases and therefore, all of the proteins that participate in such interactions may also be used in assays as described herein.

Figure 2:
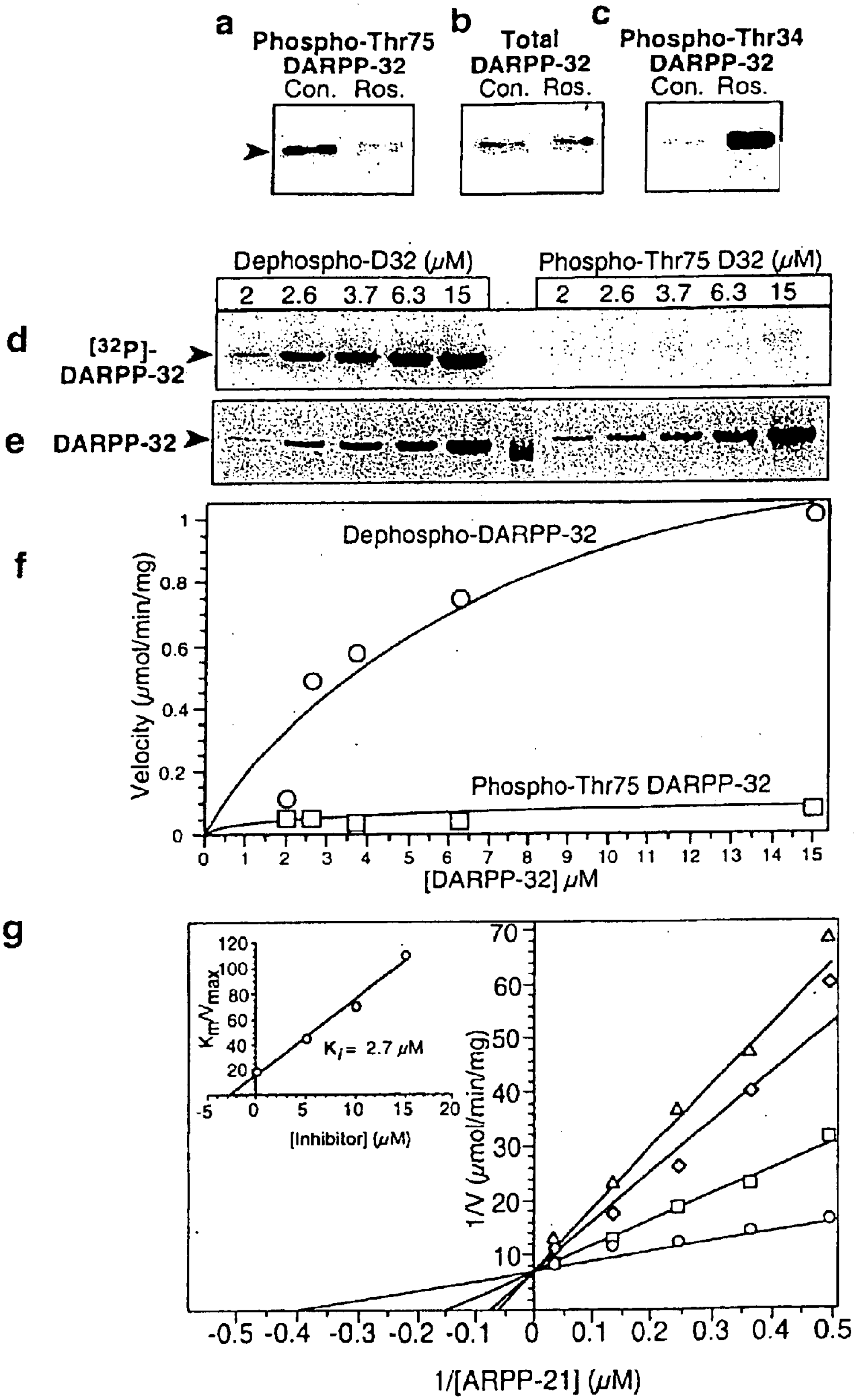
FIGS. 2*a*-2*g* show the inhibition of PKA by phospho-Thr75 DARPP-32.

Furthermore, since the phosphorylation of Thr34 DARPP-32 and Thr75 DARPP-32 appear to be mutually exclusive, potential modulators of Thr75 DARPP-32 phosphorylation can be indirectly identified employing drug assays that measure for example, an in vivo effect of phospho-Thr34 DARPP-32, such as PP1 inhibition, PKA activity, the phosphorylation state of exogenous PKA substrates (see Example 1 below and FIGS. 2 and 3) or exogenous PP1 substrates. A potential inhibitor of Thr75 DARPP-32 phosphorylation is anticipated to enhance an effect stimulated by the phosphorylation of Thr34 DARPP-32, whereas a potential agonist of Thr75 DARPP-32 phosphorylation is anticipated to inhibit an effect stimulated by the phosphorylation of Thr34 DARPP-32.

Whereas at present no first messengers, neurotransmitters, or signal transduction steps that modulate Cdk5 activity have been reported (see FIG. 4*a*), once these factors are identified they also can be used in the drug assays and screens that are exemplified herein, or alternatively in analogous assay procedures.

Protein-structure Based Design of Inhibitors of Cdk5

The atomic coordinates for the cdk2-cyclinA-ATP complex have been determined [Jeffrey et al., *Nature* 376:313–320 (1995)] which has allowed the computer generated structural model of Cdk5 complexed with Nck5a (p25) and ATP to be compiled [Chou et al., *Biochem. Biophys. Res. Comm.* 259:420428 (1999)]. Therefore, the present invention further provides a means of performing rational drug design to develop drugs that can modulate Thr75 DARPP-32 phosphorylation and thereby ameliorate dopamine related disorders. Such rational drug design can be performed using compounds that have been identified to inhibit Cdk5 as a starting point. Roscovitine, for example, has been exemplified below. Other compounds include olomucine, flavopiridol, staurosporine and paullone which are competitive inhibitors for ATP (FIG. 5). Thus, the present invention provides screens and assays to allow more specific inhibitors to be identified.

Indeed, a potential modulator of Cdk5 can be examined through the use of computer modeling using a docking program such as GRAM, DOCK, or AUTODOCK [Dunbrack et al., Folding & Design, 2:27–42 (1997)], to identify potential modulators of Cdk5. These modulators can then be tested for their effect on Thr75 DARP-32 phosphorylation. This procedure can include computer fitting of potential modulators to the Cdk5-Nck5a complex to ascertain how well the shape and the chemical structure of the potential modulator will bind to either Cdk5, Nck5a or to the Cdk5-Nck5a complex [Bugg et al., *Scientific American, Dec.*:92–98 (1993); West et al., TIPS, 16:67–74 (1995)]. Computer programs can also be employed to estimate the attraction, repulsion, and steric hindrance of the subunits with a modulator/inhibitor (e.g.,Cdk5-Nck5a complex and a potential destabilizer).

Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially compounds known to bind Cdk5, for example roscovitine, can be systematically modified by computer modeling programs until one or more promising potential analogs are identified. In addition systematic modification of selected analogs can then be systematically modified by computer modeling programs until one or more potential analogs are identified. Such analysis has been shown to be effective in the development of HIV protease inhibitors [Lam et al., *Science* 263:380–384 (1994); Wlodawer et al, *Ann. Rev. Biochem.* 62:543–585 (1993); Appelt, *Perspectives in Drug Discovery and Design* 1:23–48 (1993); *Erickson, Perspectives in Drug Discovery and Design* 1:109–128 (1993)]. Alternatively a potential modulator could be obtained by initially screening a random peptide library produced by recombinant bacteriophage for example, see above. A peptide selected in this manner could then be systematically modified by computer modeling programs as described above, and then treated analogously to a structural analog as described above.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. The de novo synthesis of one or even a relatively small group of specific compounds is reasonable in the art of drug design. The potential modulator can be placed into a standard kinase assay with Cdk5, Nck5a, ATP and DARP-32 or a fragment of DARP-32 comprising Thr75, for example.

A peptide modulator or DARPP-32 fragment can be synthesized by either standard peptide synthesis described above, or generated through recombinant DNA technology or classical proteolysis as stated above. In a particular embodiment when a suitable potential modulator is identified, a crystal can be grown which comprises the Cdk5-Nck5a complex and the potential modulator. Preferably the crystal effectively diffracts X-rays for the determination of the atomic coordinates of the protein-ligand complex to a resolution of better than 5.0 Angstroms, more preferably equal to or better than 3.5 Angstroms. Once the three-dimensional structure of the crystal are determined, the three-dimensional structure of supplemental crystals can be determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, *Acta Crystallographics ASO,* 157–163 (1994)]. Once the position and orientation are known an electron density map can be calculated using the search model to provide X-ray phases. Thereafter, the electron density is inspected for structural differences and the search model is modified to conform to the new structure.

A candidate drug can be selected by performing rational drug design with the three-dimensional structure determined for the supplemental crystal, preferably in conjunction with computer modeling discussed above. The candidate drug (e.g., a potential modulator of Cdk5) can then be assayed as exemplified above, or in situ. A candidate drug can be identified as a drug, for example, if it inhibits Cdk5 phosphorylation of Thr75 DARPP-32.

For all of the drug screening assays described herein further refinements to the structure of the drug will generally be necessary and can be made by the successive iterations of any and/or all of the steps provided by the particular drug screening assay.

The present invention also provides kits for performing the methods of the present invention. One particular kit can be used in detecting the presence of phospho-Thr75 DARP-32 protein in a cellular sample. In one such embodiment the kit comprises a predetermined amount of a detectably labeled binding partner of the phospho-Thr75 DARP-32 protein. In a particular embodiment of this type the binding partner is a phosphorylation state-specific antibody to the phospho-Thr75 DARP-32 protein. In a preferred embodiment of this type, the kit also contains a separate sample of phospho-Thr75 DARP-32 protein or fragment thereof to use as a standard. The kits can also comprise other reagents and/or written protocols.

Peptide Synthesis

Synthetic polypeptides, can also be prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield [J. Am. Chem. Soc., 85:2149–2154 (1963)], or the base-labile $N^{\alpha}$-amino protected 9-fluorenylmethoxycarbonyl (Fmoc) amino acids first described by Carpino and Han [J. Org. Chem., 37:3403–3409 (1972)].

Both Fmoc and Boc $N^{\alpha}$-amino protected amino acids can be obtained from The Rockefeller University Protein/DNA Technology Center, Fluka, Bachem, Advanced Chemtech, Sigma, Cambridge Research Biochemical, Bachem, or Peninsula Labs or other chemical companies familiar to those who practice this art. In addition, the method of the invention can be used with other $N^{\alpha}$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, IL; Fields and Noble, 1990*, Int. J. Pept. Protein Res.* 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Ca-methyl amino acids, and Na-methyl amino acids, etc.) to convey special properties. Synthetic amino acids include omithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

Traversing the Blood Brain Barrier

Whereas the present invention includes the now standard (though fortunately infrequent) procedure of drilling a small hole in the skull to administer a drug of the present invention, in a preferred aspect, the agent/drug can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier, or to docosahexaenoic acid etc. In another embodiment, the molecule can be administered intracranially or, more preferably, intraventricularly. In another embodiment, osmotic disruption of the blood-brain barrier can be used to effect delivery of agent to the brain [Nilayer et al., Proc. Natl. Acad. Sci. USA 92:9829–9833 (1995)]. In yet another embodiment, an agent can be administered in a liposome targeted to the blood-brain barrier. Administration of pharmaceutical agents in liposomes is known [see Langer, *Science* 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.] All of such methods are envisioned in the present invention.

Although some predictions have been made concerning the ability of molecules to pass through the blood-brain barrier, these predictions are at best speculative. The rate and extent of entry of a compound into the brain are generally considered to be determined primarily by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) [Glave and Hansch, *J. Pharm. Sci.* 61:589 (1972); Hansch et al., *J. Pharm. Sci.,* 76:663 (1987)]. In practice, the octanol-water partition system only provides a qualitative indication of the capability of a compound to cross the blood-brain barrier. For example, comparisons between known histamine $H_2$ receptor antagonists suggest that there is no such simple relationship between their brain penetration and octanol water partition coefficients [Young et al., *J. Med. Chem* 31:656 (1988)]. Other factors, besides the octanol-water partition influence the propensity to cross the blood-brain barrier. Comparison of the ability of histamine $H_2$ receptor antagonists to cross the blood-brain barrier suggests that brain penetration may increase with decreasing over-all hydrogen binding ability of a compound (Young et al., supra). Begley et al. [*J. Neurochem.* 55:1221–1230 (1990)] herein incorporated by reference in its entirety, have more recently examined the ability of cyclosporin A to cross the blood-brain barrier. Methodology as used by Begley et al. includes: (1) measuring the brain uptake index (BUI) with the equation for a tritiated agent compound:

$$BUI=[(\text{brain } ^3H/\text{brain } ^{14}C)/(\text{injectate } ^3H/\text{injectate } ^{14}C)]\times 100$$

where the $^{14}C$ reference compound is $^{14}C$ butanol or an analogous solvent; (2) Brain perfusion studies; (3) Intravenous bolus injection studies; and (4) Studies with cultured cerebral capillary endothelium.

Labels

Any of the potential agents and targets for the potential agents (e.g., Cdk5) or DARPP-32 (such as $^{32}P$-Thr75 phosphorylated DARPP-32) can be labeled. Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a luminescent moiety, or a fluorescent moiety including as a modified/fusion chimera of green fluorescent protein (as described in U.S. Pat. No. 5,625,048 filed Apr. 29, 1997, and WO 97/26333, published Jul. 24, 1997, the disclosures of each are hereby incorporated by reference herein in their entireties). In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70. 419–439, 1980 and in U.S. Pat. No. 4,857, 453.

Suitable enzymes include, but are not limited to, alkaline phosphatase and horseradish peroxidase. Other labels for use in the invention include magnetic beads or magnetic resonance imaging labels.

As exemplified herein, proteins can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$]-amino acids (with the tritium substituted at non-labile positions).

The present invention also provides fusion proteins comprising the phospho-Thr75 DARPP-32 protein and fragments thereof which have been "modified" i.e., placed in a fusion of chimeric peptide or protein, or labeled, e.g., to have an N-terminal FLAG-tag, or a C-terminal 6×His-tag. In a particular embodiment a phospho-Thr75 DARPP-32 fragment or full-length protein is modified to contain a marker protein such as green fluorescent protein as described in U.S. Pat. No. 5,625,048 filed Apr. 29, 1997 and WO 97/26333, published Jul. 24, 1997 (each of which are hereby incorporated by reference herein in their entireties), glutathione-S-transferase (GST) as described in Example 1 below, or a poly-histidine tag.

General Genetic Manipulations

The present invention also provides methods of expressing specific drug targets, kinases, and/or kinase substrates including vectors containing nucleic acids encoding DARPP-32 and analogs and derivatives of DARPP-32. Included are homologs of human and mouse DARPP-32 and fragments thereof, from other species. Therefore the production and use of derivatives and analogs related to DARPP-32 are within the scope of the present invention.

DARPP-32 derivatives, for example, can be made by altering encoding nucleic acid sequences by substitutions, additions or deletions including to provide for functionally equivalent molecules. Due to the degeneracy of nucleotide coding sequences, other DNA sequences which encode substantially the same amino acid sequence as a DARPP-32 gene may be used in the practice of the present invention. These include but are not limited to allelic genes, homologous genes from other species, and nucleotide sequences comprising all or portions of DARPP-32 genes which are altered by the substitution of different codons that encode the same amino acid residue within the sequence, thus producing a silent change. Likewise, the DARPP-32 derivatives of the invention include, but are not limited to, those containing, as a primary amino acid sequence, all or part of the amino acid sequence of a DARPP-32 including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gin for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding drug targets, kinases, kinase substrates such as DARPP-32 derivatives and analogs of the invention can be produced by various methods known in the art. The manipulations which result in their production can occur at the gene or protein level. For example, the cloned DARPP-32 gene sequence can be modified by any of numerous strategies known in the art [Sambrook, Fritsch & Maniatis, *Molecular Cloning: A Laboratory Manual, Second Edition* (1989) Cold Spring Harbor Laboratory Press, Cold Spring Harbor, N.Y.]. The sequence can be cleaved at appropriate sites with restriction endonuclease(s), followed by further enzymatic modification if desired, isolated, and ligated in vitro. In the production of the gene encoding a derivative or analog of DARPP-32, care should be taken to ensure that the modified gene remains within the same translational reading frame as the DARPP-32 gene, uninterrupted by translational stop signals, in the gene region where the desired activity is encoded.

Additionally, the DARPP-32-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated DARPP-32 gene product. Any technique for mutagenesis known in the art can be used, including but not limited to, in vitro site-directed mutagenesis [Hutchinson, C., et al., 1978, J. Biol. Chem. 253:6551; Zoller and Smith, 1984, DNA 3:479488; Oliphant et al., 1986, Gene 44:177; Hutchinson et al., 1986, Proc. Natl. Acad. Sci. U.S.A. 83:710], use of TAB® linkers (Pharmacia), etc. PCR techniques are preferred for site directed mutagenesis [see Higuchi, 1989, "Using PCR to Engineer DNA", in PCR Technology: Principles and Applications for DNA Amplification, H. Erlich, ed., Stockton Press, Chapter 6, pp. 61–70].

A nucleotide sequence coding for DARPP-32, a fragment of DARPP-32 or a derivative or analog thereof, including a functionally active derivative, such as a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a DARPP-32 of the invention or a fragment thereof is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding DARPP-32 and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant DARPP-32 protein of the invention, or DARPP-32 fragment, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra].

A cell containing the recombinant vector comprising the nucleic acid encoding DARPP-32 for example, can be cultured in an appropriate cell culture medium under conditions that provide for expression of DARPP-32 by the cell.

DNA fragments can be readily inserted into an expression vector consisting of appropriate transcriptional/translational control signals and the protein coding sequences. These methods may include in vitro recombinant DNA and synthetic techniques and in vivo recombination (genetic recombination).

Expression of DARPP-32 may be controlled by any promoter/enhancer element known in the art, but these regulatory elements must be functional in the host selected for expression. Promoters that may be used to control DARPP-32 gene expression are well known in the art including prokaryotic expression vectors such as the β-lactamase promoter [Villa-Kamaroff, et al., *Proc. Natl. Acad. Sci. U.S.A.,* 75:3727–3731 (1978)], or the tac promoter [DeBoer, et al., *Proc. Natl. Acad. Sci. U.S.A.,* 80:21–25 (1983)].

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene,* 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μplasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SalI, SmaI, and EcoRI cloning site, with the vector expressing both the cloned gene and DHFR; see Kaufman, *Current Protocols in Molecular Biology,* 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker, Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacI, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the bacterial DARPP-32. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors can be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.,* 267:963–967 (1992); Wu and Wu, J. Biol. Chem., 263:14621–14624 (1988); Hartmut et al., Canadian Patent Application No. 2,012,311, filed Mar. 15, 1990].

Phosphorylation State-Specific Antibodies Having Specificity for Thr75-Phosphorylated DARPP-32

According to the present invention, the Thr75-phosphorylated DARPP-32 or fragment containing Threonine-75 as produced by a recombinant source, or through chemical synthesis, proteolysis of the DARP-32 or as isolated from natural sources; and derivatives or analogs thereof, including fusion proteins, may be used as an immunogen to generate antibodies that recognize Thr75-phosphorylated DARPP-32 as exemplified below. Such antibodies include but are not limited to polyclonal, monoclonal, chimeric, single chain, Fab fragments, and a Fab expression library. The Thr75-phosphorylated DARPP-32 antibodies of the invention may be cross reactive, that is, they may recognize a Thr75-phosphorylated DARPP-32 derived from a different source. Polyclonal antibodies have greater likelihood of cross reactivity. Alternatively, an antibody of the invention is preferably specific for the Thr75-phosphorylated DARPP-32 having an amino acid sequence of SEQ ID NO: 1.

Various procedures known in the art may be used for the production of polyclonal antibodies to Thr75-phosphorylated DARPP-32 or derivative or analog thereof. For the production of antibody, various host animals can be immunized by injection with the Thr75-phosphorylated DARPP-32, or a derivative (e.g., or fusion protein) thereof, including but not limited to rabbits, mice, rats, sheep, goats, etc. In one embodiment, the Thr75-phosphorylated DARPP-32 can be conjugated to an immunogenic carrier, e.g., bovine serum albumin (BSA) or keyhole limpet hemocyanin (KIM). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.* As exemplified below a phosphorylation state specific antibody was obtained following the procedure of Czemik et al. [in Regulatory Protein Modification (ed., H. C. Hemming, Jr) Pg. 219–246 (Humana, Tototwa N.J. (1997)].

For preparation of monoclonal antibodies directed toward the Thr75-phosphorylated DARPP-32, any technique that provides for the production of antibody molecules by continuous cell lines in culture may be used. These include but are not limited to the hybridoma technique originally developed by Kohler and Milstein [Nature, 256:495–497 (1975)], as well as the trioma technique, the human B-cell hybridoma technique [Kozbor et al., Immunology Today, 4:72 (1983); Cote et al., *Proc. Natil. Acad. Sci. U.S.A.,* 80:2026–2030 (1983)], and the EBV-hybridoma technique to produce human monoclonal antibodies [Cole et al., in *Monoclonal Antibodies and Cancer Therapy, Alan R. Liss, Inc., pp.* 77–96 (1985)]. In an additional embodiment of the invention, monoclonal antibodies can be produced in germ-free animals utilizing the technology taught in PCT/US90/02545. In fact, according to the invention, techniques developed for the production of "chimeric antibodies" [Morrison et al., *J. Bacteriol.,* 159:870 (1984); Neuberger et al., *Nature,* 312:604–608 (1984); Takeda et al., Nature, 314:452–454 (1985)] by splicing the genes from a mouse antibody molecule specific for a Thr75-phosphorylated DARPP-32 together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce e.g., Thr75-phosphorylated DARPP-32-specific single chain antibodies. An additional embodiment of the invention utilizes the techniques described for the construction of Fab expression libraries [Huse et al., *Science,* 246:1275–1281 (1989)] to allow rapid and easy identification of monoclonal Fab fragments with the desired specificity for Thr75-phosphorylated DARPP-32.

Antibody fragments which contain the idiotype of the antibody molecule can be generated by known techniques. For example, such fragments include but are not limited to: the $F(ab')_2$ fragment which can be produced by pepsin digestion of the antibody molecule; the F(ab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of Thr75-phosphorylated DARPP-32, one may assay generated hybridomas for a product which binds to the Thr75-phosphorylated DARPP-32 fragment containing such epitope and choose those which do not cross-react with Thr75-phosphorylated DARPP-32. For selection of an antibody specific to a Thr75-phosphorylated DARPP-32 from a particular source, one can select on the basis of positive binding with Thr75-phosphorylated DARPP-32 expressed by or isolated from that specific source.

The foregoing antibodies can be used in methods known in the art relating to the localization and activity of the Thr75-phosphorylated DARPP-32, e.g., for Western blotting, imaging Thr75-phosphorylated DARPP-32 in situ, measuring levels thereof in appropriate physiological samples, etc. using any of the detection techniques mentioned herein or known in the art.

The particular steps involved in the generation of phosphorylation state-specific antibodies (PSSAb) to Thr75 DARPP-32 exemplified below are shown in FIGS. 6A–6F [see Czemik et al., in *Regulatory Protein Modification* (ed., H. C. Hemming, Jr) Pg. 219–246 (Humana, Tototwa N.J. (1997) hereby incorporated by reference in its entirety]. The particular phospho-peptide used to generate the P-Thr75 DARPP-32 phosphorylation state-specific antibody used in Example 1 below has the amino acid sequence of CAYTPPSLK, in which the threonine residue was chemically phosphorylated. Thus a selected phospho-peptide that corresponds to a fragment of the phosphoprotein of interest containing the particular phosphorylated amino acid residue of interest can be prepared (e.g., by peptide synthesis). The phospho-peptide is preferably conjugated to a carrier protein using an appropriate crosslinker and then inoculated into a non-human animal subject (e.g., a sheep or a rabbit). The inoculated non-human animal can then be boosted and bled as required to obtain sera containing the desired antibody. Primary screening (e.g., by immunoblotting) of the antisera is performed to identify an antibody that is specific for the particular phosphoprotein (i.e., phospho-Thr75 DARPP-32). Preferably, the phospho-specific antibody is then purified. One such method includes using Protein A and phospho/dephosphopeptide affinity chromatography [see Czemik et al., in Regulatory Protein Modification (ed., H. C. Hemming, Jr) Pg. 219–246 (Humana, Tototwa N.J. (1997)].

Administration

According to the invention, the component or components of a therapeutic composition of the invention may be introduced parenterally, topically, or transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, *ibid*., pp. 317–327; see generally *ibid*.]. To reduce its systemic side effects, this may be a preferred method for introducing the agent.

In yet another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used [see Langer, supra; Sefton, CRC *Crit. Ref Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release, Langer and Wise* (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the brain, thus requiring only a fraction of the systemic dose [see, e.g., Goodson, in Medical Applications of ControlledRelease, supra, vol. 2, pp. 115–138 (1984)).

Other controlled release systems are discussed in the review by Langer [Science 249:1527–1533 (1990)].

Pharmaceutical Compositions: In yet another aspect of the present invention, provided are pharmaceutical compositions of the above. Such pharmaceutical compositions may be for administration for injection, or for oral, topological, nasal or other forms of administration. In general, comprehended by the invention are pharmaceutical compositions comprising effective amounts of the agents of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

Oral Delivery: Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the agent and inert ingredients which allow for protection against the stomach environment, and release of the biologically active material in the intestine.

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the agent are for instance the fatty acids oleic acid, linoleic acid and linolenic acid.

Controlled release oral formulation may be desirable. The agent could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Nasal Delivery. Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament: In yet another aspect of the present invention, methods of treatment and manufacture of a medicament are provided. Conditions alleviated or modulated by the administration of the present derivatives are those indicated above.

Dosages. For any of the agents, as further studies are conducted, information will emerge regarding appropriate dosage levels for treatment of various conditions in various patients, and the ordinary skilled worker, considering the therapeutic context, age and general health of the recipient, will be able to ascertain proper dosing. Generally, for intravenous injection or infusion, dosage may be lower. The dosing schedule may vary, depending on the circulation half-life, and the formulation used.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Cdk5 Phosphorylation of DARPP-32 Modulates Dopamine Signaling in Neurons

Introduction

Numerous first messengers modulate the phosphorylation and dephosphorylation of DARPP-32 at Threonine-34 in intact cells, thereby altering PP1 activity and regulating the states of phosphorylation and activities of a variety of downstream physiological effectors. The biological significance of this pathway has been demonstrated using mice containing a targeted deletion of the DARPP-32 gene (DARPP-$32^{-/-}$), which exhibit a dramatically altered biochemical, electrophysiological, and behavioral phenotype [U.S. Pat. No. 5,777,195, Issued Jul. 7, 1998; Fienberg et al., *Science* 281:838–842 (1998), the contents of each are hereby incorporated by reference herein, in their entireties].

The amino acid sequence of DARPP-32 also contains consensus phosphorylation sites for proline-directed kinases including Cdk5, a cyclin-dependent kinase family member, that together with its non-cyclin cofactor, Nck5a (p35), is present in post-mitotic neurons expressing high levels of DARPP-32 [Lew et al., *Nature* 371:423426 (1994); Tsai et al. *Nature* 371:419423 (1994)].

Results

Figure 1:
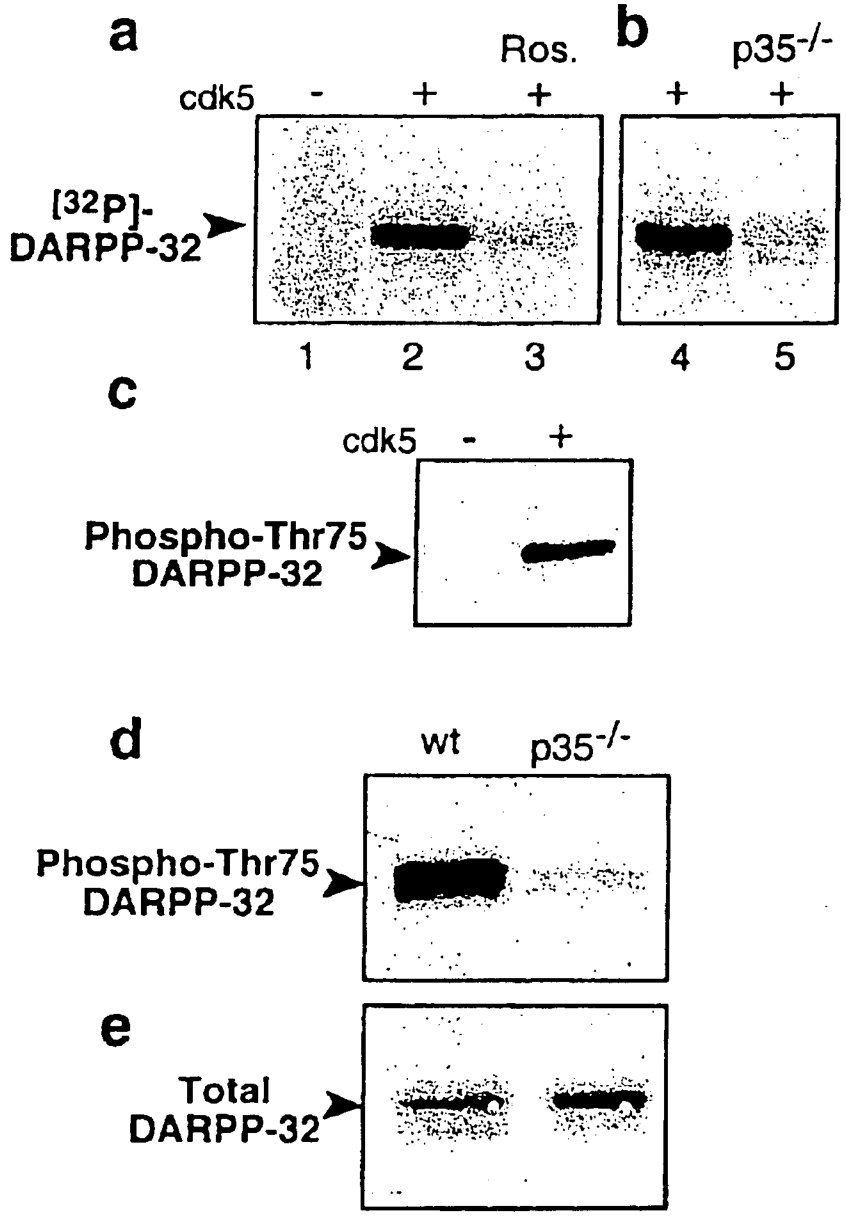
FIGS. 1*a*–1*e* show the phosphorylation of DARPP-32 at Thr75 by Cdk5 in vitro and in vivo.

Cdk5, immunoprecipitated from mouse striatal homogenates, phosphorylated purified DARPP-32 in vitro (FIGS. 1*a* and 1*b*). Phosphorylation was greatly reduced by the addition of the specific Cdk5 inhibitor roscovitine [Meijer et al., Eur. J. Biochem. 243:527–536 (1997)]. DARPP-32 was much less efficiently phosphorylated by Cdk5 immunoprecipitated from striatal homogenates of $p35^{-/-}$ ($Nck5a^{-/-}$) mice (FIG. 1*b*).

Purified DARPP-32 was phosphorylated in vitro by recombinant GST-Cdk5 (FIG. 1*c*) as well as by recombinant cdk1. Proteolytic digestion, HPLC purification, phosphopeptide mapping, microsequencing, and MALDI-TOF mass spectrometry analysis indicated that the site of phosphorylation by either Cdk5 or cdk1 was Threonine-75 (Thr75). A recombinant protein containing a Thr75Ala mutation was not phosphorylated, indicating that Thr75 is the only site phosphorylated by Cdk5 and cdk1. In contrast, MAP kinase, another proline-directed kinase, did not phosphorylate DARPP-32 at Thr75.

To directly monitor DARPP-32 phosphorylation by Cdk5 in vitro and in brain tissue, a phosphorylation state-specific antibody was generated which detected DARPP-32 only in its Thr75 phosphorylated state (FIG. 1*c*). DARPP-32 was phosphorylated at Thr75 in freshly prepared adult mouse striatal tissue (FIGS. 1*d* and 1*e*). Comparison of phospho-Thr75 and total DARPP-32 standards indicated that the stoichiometry of Thr75 DARPP-32 phosphorylation was −0.26 under basal conditions. The level of DARPP-32 in striatal neurons has been estimated to be −50 μM [Ouimet et al., Brain Res. 808:8–12 (1998)). Therefore, the basal concentration of phospho-Thr75 DARPP-32 was −13 μM. The basal level of phospho-Thr75 DARP-32 was reduced by 75% in p35' mouse striatum, whereas the total level of DARPP-32 was unaffected (compare FIG. 1*d* with FIG. 1*e*).

The role of DARPP-32 phosphorylated at Thr75 was assessed in striatal slices from adult mice. Inhibition of Cdk5 by roscovitine treatment reduced phospho-Thr75 DARPP-32 without affecting the total level of DARPP-32 (FIGS. 2*a* and 2*b*). Remarkably, roscovitine treatment increased phospho-Thr34 DARPP-32 (FIG. 2*c*). The results suggested a reciprocal relationship between the two phosphorylation sites. A biochemical approach was used to determine the mechanism underlying this relationship. The ability of PKA to phosphorylate Thr34 DARPP-32 in vitro was virtually abolished by prior phosphorylation at Thr75 (FIGS. 2*d*-2*f*). To test the possibility that this effect was due to phospho-Thr75 acting as an inhibitor of PKA, the ability of the purified catalytic subunit of PKA to phosphorylate several other well-characterized substrates was assessed in the absence and presence of added phospho-Thr75 DARPP-32. The presence of 15 μM phospho-Thr75 DARPP-32 resulted in a dramatic reduction in the rates of phosphorylation by PKA of inhibitor-1 (a DARPP-32 homologue), ARPP-21 (a PKA substrate enriched in the basal ganglia [Hemmings et al., *J. Biol. Chem.* 264:7726–7733 (1989)], synapsin I, and histone H1. Kinetic analysis of ARPP-21 phosphorylation in the presence of various concentrations of phospho-Thr75 DARPP-32 indicated that phospho-Thr75 DARPP-32 inhibited PKA by a linear competitive single site mechanism (FIG. 2*g*). A $K_i$ value of 2.7 μM was derived from a secondary plot of the kinetic data (FIG. 2*g*, insert).

To determine whether phospho-Thr75 DARPP-32 inhibits PKA in intact neurons, phosphorylation of known substrates was assessed in mouse striatal slices treated with roscovitine to inhibit Cdk5. Roscovitine increased phosphorylation of the GluR1 subunit of the AMPA-type glutamate receptor by 3.2±0.5 fold (n=7), as assessed using an antibody specific for phospho-Ser845, a PKA phosphorylation site [Roche et al., Neuron 16:1179–1188 (1996)] (FIG. 3*a*). A roscovitine-induced increase in phospho-Ser845 GluR1 was not observed in striatal slices from adult $DARPP-32^{-/-}$ mice [U.S. Pat. No. 5,777,195, Issued Jul. 7, 1998; Fienberg et al., *Science* 281:838–842 (1998)), providing strong support for the involvement of phospho-Thr75 in this action of roscovitine. Total GluR1 levels were unaffected. Similar results (2.5±0.2 fold, n=2) for wildtype and $DARPP-32^{-/-}$ mice were observed for phosphorylation of ARPP-16 (FIG. 3*b*), a PKA substrate enriched in striatum [Horiuchi et al., *J. Biol. Chem.* 265:9476–9484 (1990)]. These results indicate that regulation by Cdk5 of the phosphorylation of Thr75 DARPP-32 has a major effect on PKA activity in intact cells.

Dopamine achieves many of its effects in neurons by activation of the D1 class of dopamine receptors, which are positively coupled to the activation of PKA. To determine whether phospho-Thr75 DARPP-32 modulates the actions of dopamine in intact cells, the ability of a D1 receptor agonist (SKF 81297) to induce phosphorylation of substrates for PKA was compared in wildtype and $p35^{-/-}$ mice. For this purpose, the state of phosphorylation of GluR1, DARPP-32, ARPP-21, and ARPP-16 was determined using phosphorylation state-specific antibodies. SKF 81297 increased the phosphorylation of each of these substrates in the wildtype mice, and did so to an even greater extent in the $p35^{-/-}$ mice (FIGS. 3*c*-3*f*). No significant difference was observed between wildtype and $p35^{-/-}$ mice in basal levels of phosphorylation of any of these substrates. These data indicate that Cdk5 phosphorylation of DARPP-32 at Thr75 is capable of modulating dopamine signaling in the striatum.

The physiological consequence of PKA inhibition by phospho-Thr75 DARPP-32 was also assessed. For this purpose, voltage-gated $Ca^{2+}$ currents, which are known to be regulated by PKA [Surmeier et al., Neuron 14:385–397 (1995); Gray et al., *Curr. Opin. Neurobiol.* 8:330–334 (1998)], were analyzed using patch-clamp recordings of dissociated striatal neurons (FIGS. 3*g* and 3*h*). Application of roscovitine (10 μM) enhanced whole-cell $Ca^{2+}$ current in wildtype neurons (9.7% ±1.0%, n=7). This effect was virtually abolished in neurons from DARPP-32 knockout mice (1.6±0.3%, n=5, p<0.01, paired t test). These data indicate that regulation of the state of phosphorylation of Thr75 DARPP-32 can modulate the physiological state of neurons in the striatum.

The specificity of intracellular signaling can be controlled by scaffolding and anchoring molecules so that kinases as well as phosphatases are localized to their substrates (Pawson et al., *Science,* 278:2075–2080 (1997)]. Moreover, protein kinases and protein phosphatases can directly associate in signaling modules [Westphal et al., *J. Biol. Chem.* 274:689–692 (1999); Klauck, *Science* 271:1589–1592 (1996)]. The data presented here show that, through phosphorylation of distinct sites, DARPP-32 can regulate both classes of activity (FIG. 4). This dual action appears especially important in regulating the efficacy of dopaminergic neurotransmission. These results also indicate a novel role for Cdk5 in the control of the actions of dopamine. The ability of one protein to regulate both a major protein kinase and a major protein phosphatase represents a new mechanism by which cell signaling pathways may be integrated.

EXAMPLE 2

CDK5 Regulates Action of Chronic Cocaine

Introduction

Cocaine, is a psychomotor stimulant extracted from the native South American plant, Erythroxylon coca, that was introduced to the general public as a therapeutic agent by the medical community in the late 19th century [Freud et al., Centralblattar die Gesellshaft Therapie 2:289–314 (1884); reprinted in English, I. *Subst. Abuse Treatment,* 206–217 (1984)]. Widespread cocaine abuse today represents a major world public health problem having a serious overall impact on society [Higgins and Katz, Cocaine Abuse: Behavior, Pharmacology, and Clinical Applications (Academic Press, New York, 1998)]. Cocaine enhances dopamine neurotransmission by blocking dopamine reuptake at axon terminals innervating medium spiny neurons in the caudatoputamen and nucleus accumbens, which together comprise the striatum. Cocaine addiction is thought to stem, in part, from neural adaptations that act to maintain equilibrium by countering the effects of repeated drug administration [Nestler and Aghajanian, Science 278:58–63 (1997); Berke and Hyman, Neuron 25:515–532 (2000); Koob and Le Moal, Science 278:52–57 (1997)]. Chronic exposure to cocaine upregulates several transcription factors that alter gene expression and could mediate such compensatory neural and behavioral plasticity [Kelz et al., Nature 401:272–276 (1999); Nestler et al., Brain Res. 835:10–17 (1999); Hope et al., Neuron 13:1235–1244 (1994); Carlezon et al., *Science* 282:2272–2275 (1998)]. One such transcription factor is ΔFosB, a highly stable protein that persists in striatum long after cessation of cocaine exposure [Hiroi et al., *Proc. Natl. Acad. Sci. USA* 94:10397–10402 (1997)]. Mice with altered ΔFosB expression exhibit abnormal behavioral responses to cocaine [Kelz et al., *Nature* 401:272–276 (1999); Hiroi et al., *Proc. Natl. Acad. Sci. USA* 94:10397–10402 (1997)].

Methods

For cDNA expression arrays, total RNA was isolated with the RNAqueous phenol-free total RNA isolation kit (Ambion) from dissected striatal tissue from either control mice carrying only the NSE-tTA gene (−ΔFosB) or ΔFosB-inducible transgenic mice carrying both Tetop-ΔFosB and NSE-tTA genes, which had been fed 100 mg/l doxycycline to inhibit transgene expression, followed by 12 weeks in the absence of doxycycline (+ΔFosB). ΔFosB induction was observed by 3 weeks (Chen et al., *Mol. Pharmacol.* 54:495–503 (1998)]. Poly(A)+ RNA was isolated from total RNA using an Oligotex mRNA isolation kit (Qiagen) and used as template for synthesis of $^{32}$P-labeled cDNA probes. The probes were hybridized to Atlas cDNA expression arrays containing 588 genes (Clontech). Probes were hybridized and chips were washed according to the manufacturer's suggestions. Radiographic images were generated using a Storm PhosphorImager (Molecular Dynamics).

ΔFosB-inducible transgenic mice were either fed 100 mg/i doxycycline or denied doxycycline for 12 weeks. Adult male Sprague-Dawley rats initially weighing between 160–240 g were injected with cocaine or vehicle (i.p., 20 mg/kg, 9% NaCl) at the same time each day for 8 days. All analyses were initiated 12 hr after the final dose. For in situ hybridization studies, [α-$^{35}$S]UTP-labeled riboprobes were prepared by in vitro transcription from cDNA clones corresponding to full-length clones of rat Cdk5 [Zheng et al., *J. Neurobiol.* 35:141–159 (1998)]. Cryostat sections were prepared and hybridized as previously described. After hybridization, the sections were exposed to Biomax MR film (Kodak) for 2–6 days. All autoradiograms were analyzed with a Microcomputer Imaging Device system (M4, Imaging Research, Inc.) as described elsewhere [Le Moine and Bloch, *J. Comp. Neurol.* 355:418426 (1995)]. Statistical analyses of the data were performed using two-tailed unpaired Student's t test. Striatal tissue was rapidly dissected on ice and homogenized in boiling lysis buffer containing 1% SDS and 50 mM sodium flouride with sonication. Striatal slice preparation and treatment were conducted as previously described [Example 1, Bibb et al., *Nature* 402:669–671 (1999); Nishi et al., *J. Neurosci* 17:8147–8155 (1997)]. Use of antibodies to phospho-Thr34 DARPP-32 [Snyder et al., *J. Neurosci* 12:3071–3083 (1992)], phospho-Thr75 DARPP-32 [Example 1, Bibb et al., *Nature* 402:669–671 (1999)], phospho-Ser55 ARPP-21 (Caporaso et al., *Neuropharmacology* 39:1637–1644 (1999)], phospho-Ser88 ARPP-16 [Example 1, Bibb et al., *Nature* 402:669–671 (1999)], and phospho-Ser845 GluR1 [Lee et al., *Neuron* 21:1151–1162 (1998)] for immunoblotting was performed as previously described.

Drug-induced alterations in cocaine sensitization were measured in adult male Sprague-Dawley rats according to published procedures for surgery, drug infusion, apparatus, and behavioral methods [Horger et al., *J Neuroscience* 19:4104155 (1999); Taylor and Horger, Psychopharmacology 142:31–40 (1999)]. Coordinates for the nucleus accumbens were anterior-posterior 1.7 from bregma, medial-lateral ±1.5 from the midline, dorso-ventral −6.0 from skull [Paxinos and Watson, *The rat brain in sterotaxic coordinates* (Academic Press, New York, 1982)].

Doses of cocaine hydrochloride (15 mg/kg i.p. in sterile 0.9% sodium chloride) were chosen to produce a moderate response to cocaine over successive days. Roscovitine, olomoucine, and iso-olomoucine (Alexis Biochemicals) doses (40 nmol/0.5 μl) were based on previous studies using intra-cerebral infusions of cAMP analogs [Punch et al, *J. Neurosci.* 17:8520–8527 (1997)]. Drugs were dissolved in sterile phosphate buffered saline containing 50% DMSO. Intracerebral microinfusions were made bilaterally in volumes of 0.5 μl over a period of 2 min with an additional 2 min allowed to elapse prior to removal of the infusion needles and replacement of the stylettes. One week after surgery and 2 days after habituation to the locomotor chambers, subjects received 5 daily injections of cocaine (15 mg/kg, i.p.) or saline 20 min after bilateral intra-accumbens vehicle, roscovitine, olomoucine, or iso-olomoucine infusions. Drugs were given at the same time each day. Subjects were then placed into the chambers and activity was monitored for 60 min.

For electrophysiological studies [Surmeier et al., *Neuron* 14:385–397 (1995)], acutely dissociated striatal neurons were prepared as previously described. Whole-cell recordings of voltage-gated AMPA/kainate-activated current (100 μM kainate) were measured using standard whole-cell voltage-clamp techniques [Hamill et al., *Pflüegers Arch.* 391:85–100 (1981)]. Summary data are presented in box plot format [J. W. Tukey, *Exploratory Data Analysis* (Addison-Wesley, Menlo Park, Calif., 1977)].

Results

Figure 8:
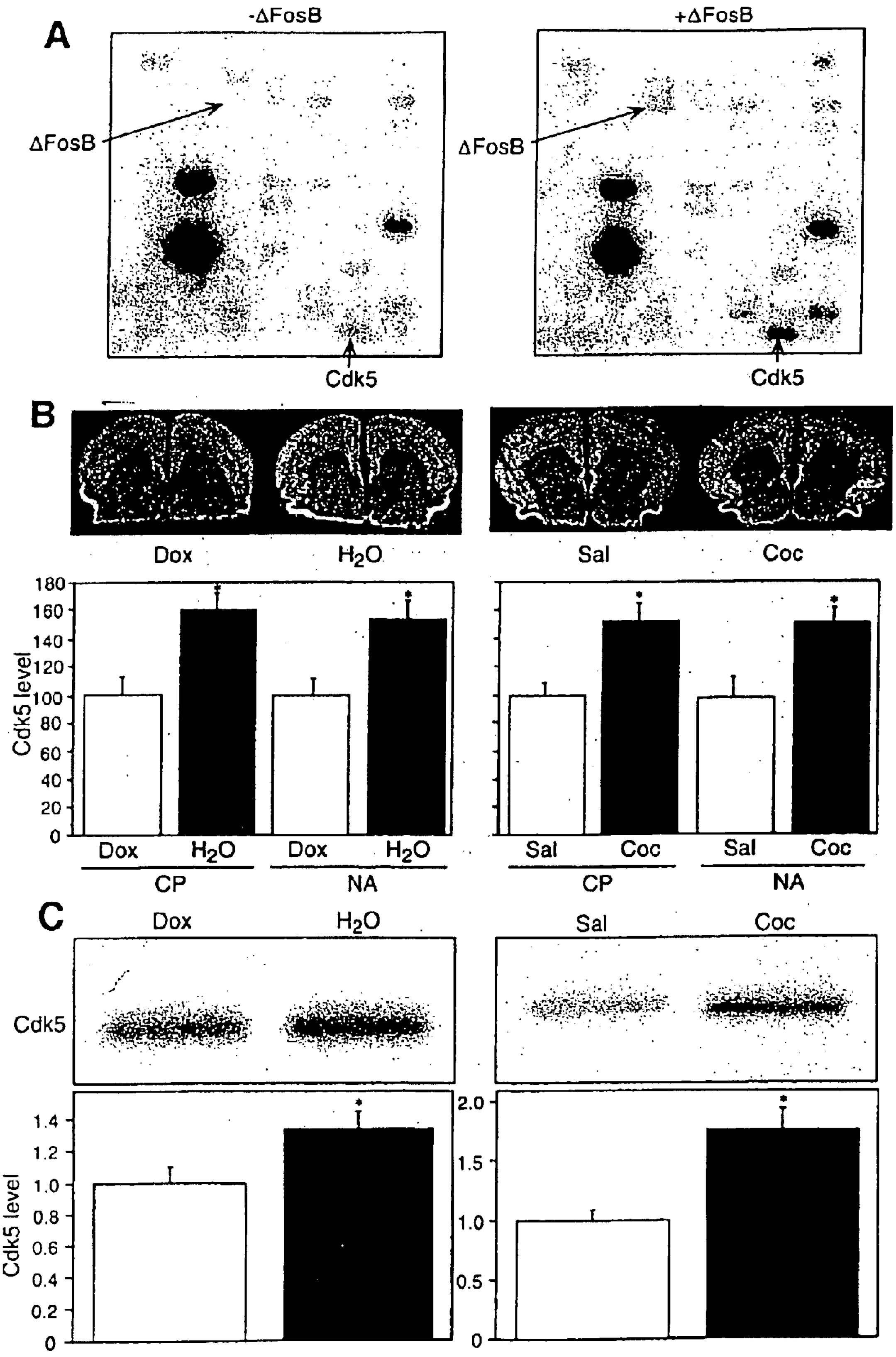
FIGS. 8A–8C show the increased expression of Cdk5 in inducible transgenic mice overexpressing ΔFosB and in rats chronically treated with cocaine.

Transgenic mice displaying inducible and targeted expression of ΔFosB in the nucleus accumbens and caudatoputaman were engineered [Chen et al., Mol. Pharmacol. 54:495–503 (1998), see Methods above]. Analysis of cDNA expression array profiles from mice overexpressing ΔFosB indicated that the neuronal protein kinase Cdk5 was a downstream target gene for ΔFosB in these brain regions (FIG. 8A). This effect was confirmed by quantitative in situ hybridization analyses of coronal brain sections from mice that did ($H_2O$) or did not (Dox) overexpress ΔFosB (FIG. 8B, left). Increased Cdk5 mRNA expression in response to ΔFosB accumulation was evident in both the caudatoputaman (160.0±14.2%, $p<0.05$) and the nucleus accumbens (152.6±12.9%, $p<0.05$). Adult rats injected with cocaine for 8 days also showed elevated Cdk5 mRNA levels in the caudatoputamen (151.8±11.8%, $p<0.05$) and nucleus accumbens (150.5±10.0%, $p<0.05$) in comparison to animals injected with saline (FIG. 8B). Increased Cdk5 protein levels were also observed in striatal tissue dissected from transgenic ΔFosB-expressing mice (130 t 10%, p<0.05) and from rats exposed chronically to cocaine (180±20%, p<0.05) compared to control animals (FIG. 8C). These results indicated that Cdk5 is a downstream target of chronic cocaine exposure and raised the possibility that this protein kinase is involved in the behavioral effects of cocaine.

Figure 9:
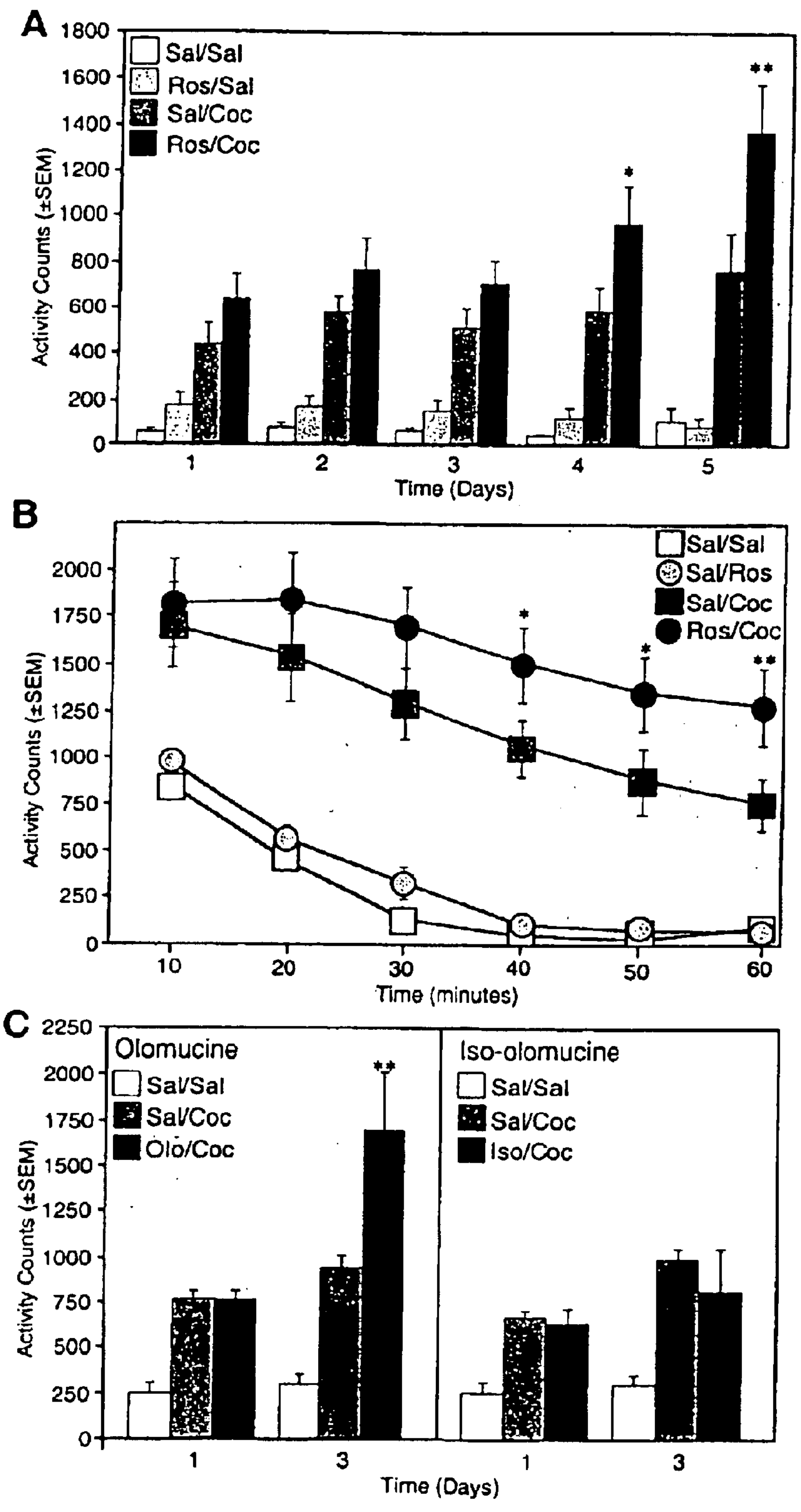
FIGS. 9A–9C show the effect of Cdk5-inhibitors on locomotor behavioral response to repeated cocaine injections.

A characteristic behavioral effect of cocaine is potentiation of locomotor activity. To determine the possible contribution of elevated Cdk5 levels to long-lasting alterations in this behavior, the effects of daily intra-accumbens infusions of a potent Cdk5 inhibitor, roscovitine [Meijer et al., Eur. J. Biochem. 243:527–536 (1997)], on cocaine-induced locomotor activity were examined over a 60 min period daily for five days. Roscovitine infusions did not significantly affect locomotor responses to initial cocaine administration. However, roscovitine markedly potentiated the locomotor effects of repeated cocaine exposures. This was evident as an augmentation of cocaine's effects over successive days of injections (FIG. 9A). By day 4, significant differences were observed between the saline/cocaine and roscovitine/cocaine groups. By day 5, mean cocaine-induced activity rates for roscovitine-infused animals were almost double those measured for vehicle-infused animals. This effect of roscovitine was most evident at 40–60 min after cocaine administration (FIG. 9B), indicating that roscovitine prolonged cocaine-induced increases in locomotor activity. Repeated intra-accumbens infusions of a less selective Cdk5 inhibitor, olomoucine [Abraham et al., Biol. Cell 83:105–120 (1997)], also potentiated cocaine's locomotor effects. This action was similar to that produced by roscovitine, except that a dramatic behavioral effect was already observed on day 3 (FIG. 9C). In response to drug treatment on days 4 and 5, olomoucine-treated animals exhibited stereotypy, which is known to compete with increases in locomotor activity, [see Hiroi et al., *Proc. Natl. Acad. Sci. USA* 94:10397–10402 (1997)]; these results are consistent with enhanced sensitization to repeated doses of cocaine in the presence of a Cdk5 inhibitor. In contrast, intra-accumbens infusions of the inactive congener, iso-olomoucine, failed to enhance either locomotor or stereotypic responses to cocaine (FIG. 9C). These behavioral findings indicate that cocaine-induced increases in Cdk5 levels may serve a homeostatic function to dampen responses to subsequent drug exposure.

Figure 10:
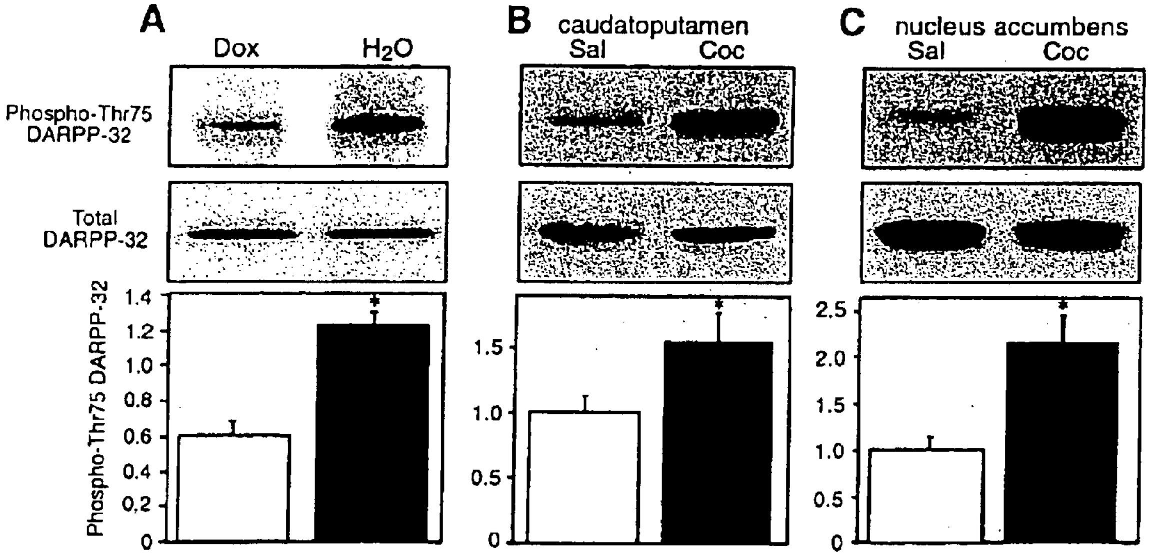
FIGS. 10A–10C show increased phosphorylation of DARPP-32 by Cdk5 in inducible transgenic mice overexpressing ΔFosB and in rats chronically treated with cocaine.

One way by which Cdk5 could downregulate the psychomotor effects of chronic cocaine is through regulation of dopamine signaling. Cdk5 phosphorylates a key molecule invloved in striatal dopamine signaling, DARPP-32 (Dopamine and cyclic AMP-Regulated Phospho-Protein, Mr 32 kDa), at threonine-75 (Thr75) [Example 1, Bibb et al., *Nature* 402:669–671 (1999)]. Therefore, the possibility was examined as to whether the increases in Cdk5 levels brought about either byΔFosB overexpression in mice or by chronic exposure to cocaine in rats. Thus, these increases in Cdk5 levels could be reflected in alterations in the state of phosphorylation of DARPP-32 at Thr75. Increased levels of phospho-Thr75 DARPP-32 were indeed observed in striatal tissue dissected from transgenic mice overexpressing ΔFosB (FIG. 10A). In rats subjected to chronic cocaine administration the levels of phospho-Thr75 DARPP-32 were increased in both the caudatoputamen and nucleus accumbens (FIGS. 10B and 10C). In contrast, total levels of DARPP-32 were unaffected by these treatments.

Figure 11:
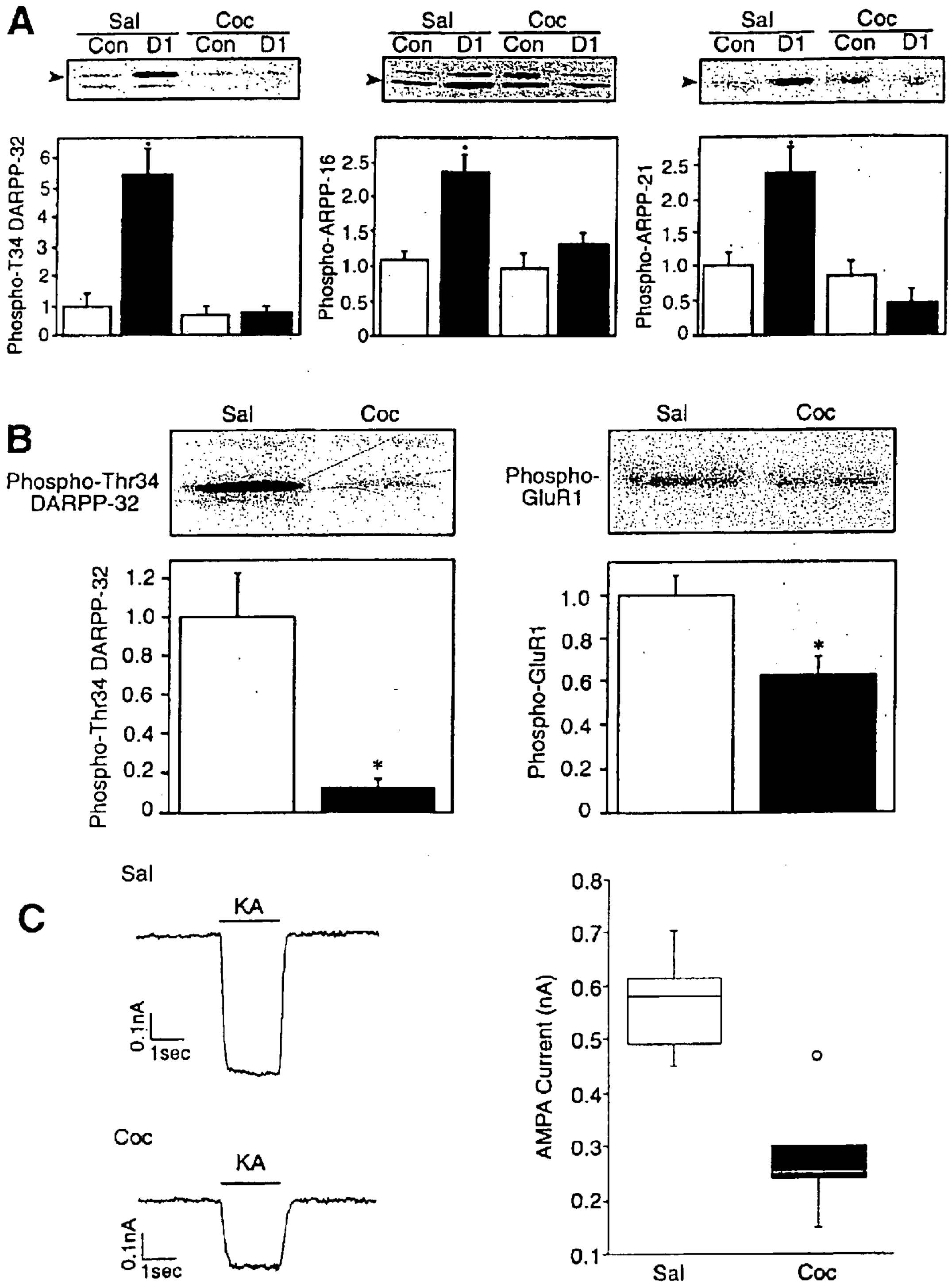
FIGS. 11A–11C show the effects of chronic cocaine exposure on dopamine/PKA signalling in the striatum.

Cdk5-dependent phosphorylation of DARPP-32 at Thr75 reduces the efficacy of dopamine/PKA/DARPP-32/PP-1 signaling [Example 1, Bibb et al., Nature 402:669–671 (1999)]. To further test the possibility that the chronic cocaine-dependent regulation of Cdk5 activity was biologically relevant, various aspects of this signaling pathway were examined. Treatment of striatal slices from saline-injected rats with the $D_1$ receptor agonist, SKF 81297, is known to increase PKA-dependent phosphorylation of DARPP-32 [Snyder et al., *J. Neurosci* 12:3071–3083 (1992)], ARPP-16 [Dulubova et al., *J. Neurochem.* (submitted) (2000)], and ARPP-21 [Caporaso et al., *Neuropharmacology* 39:1637–1644 (1999)]. These effects of the $D_1$ agonist were abolished in striatal slices from rats exposed to chronic cocaine (FIG. 11A). Decreased PKA-dependent phosphorylation of DARPP-32 (at Thr34) and of the GluR1 subunit of the AMPA-type glutamate receptor (at Ser845) was observed in striatal tissue dissected from rats chronically treated with cocaine (FIG. 11B). Consistent with the ability of PKA-dependent phosphorylation of GluR1 to increase AMPA channel conductance [Roche et al., *Neuron* 16:1179–1188 (1996)], reduced peak amplitudes of AMPA-evoked $Ca^{2+}$ currents in striatal neurons from chronic cocaine-treated rats were observed (FIG. 11C). These results expand upon the observation that nucleus accumbens neurons from psychomotor stimulant-treated rats were less sensitive to the rate-enhancing effects of glutamate [White et al., *J. Pharmacol. Exp. Ther.* 273:445–454 (1995)].

While total levels of PKA catalytic subunit are increased in the nucleus accumbens after chronic cocaine administration [Nestler and Aghajanian, Science 278:58–63 (1997); Self and Nestler, Annu. Rev. Neurosci. 18:463–495 (1995)], the level of PKA activity within accumbens neurons in the intact brain has not been previously assessed. The results presented here indicate that chronic exposure to cocaine is, in fact, associated with a decrease in PKA activity, as evidenced by a reduction in the ability of a $D_1$ agonist to stimulate PKA-dependent phosphorylation of DARPP-32, ARPP-16, and ARPP-21, by lowered basal phosphorylation of DARPP-32 (at Thr34) and GluR1 (at Ser845), and by decreased conductance of the AMPA channel. The attenuation of PKA-dependent signaling by chronic cocaine can be explained by increased Cdk5-dependent phosphorylation of DARPP-32 on Thr75. Viewed in this way, the increase in total PKA levels observed in earlier studies represents a compensatory change secondary to the decrease in PKA activity.

There is now considerable evidence that the D1 receptor plays an important role in mediating the behavioral effects of cocaine [White et al., *J. Pharmacol. Exp. Ther.* 273:445–454 (1995); Self and Nestler, Annu. Rev. Neurosci. 18:463–495 (1995); Dreher and Jackson, Brain Res. 487:267–277 (1989) ;Xu et al., Cell 79:945–955 (1994); Henry and White, J. Pharmacol. Exp. Ther. 258:882–890 (1991)]. Taken together, the data reported here support a biochemical scheme in which repeated exposure to cocaine causes accumulation of ΔFosB, which in turn results in increased expression of Cdk5; increased Cdk5-dependent phosphorylation of DARPP-32 at Thr75 then reduces PKA activity and attenuates $D_1$-dopamine receptor signaling. In support of the behavioral relevance of this scheme, mice lacking the DARPP-32 gene [Fienberg et al., *Science* 281:838–842 (1998); Hiroi et al., Eur. J. Neurosci. 11:1114–1118 (1999)] and rats treated with Cdk5 inhibitors (FIG. 9) both exhibit enhanced behavioral responses to chronic administration of cocaine. The ability of intra-accumbens infusions of Cdk5 inhibitors to potentiate the locomotor effects of repeated cocaine administration suggests that the Cdk5/DARPP-32 pathway serves a negative feedback homeostatic role with respect to the behavioral effects of cocaine. Other actions of Cdk5 may also contribute to the behavioral effects of cocaine [Patrick et al., Nature 402:615–621 (1999); Nikolic et al., Genes Dev. 10:816–825 (1996); Ohshima et al., *Proc. Natl. Acad. Sci. USA* 93:11173–11178 (1996); Chae et al., *Neuron* 18:2942 (1997)].

Various publications are cited herein including those below, the disclosures of which are incorporated by reference in their entireties.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

What is claimed is:

1. A method for treating dopamine dysregulation in an individual comprising administration to the individual an agent that is a member of a compound selected from the group consisting of an indirubin and a paullone, wherein said agent binds to Cdk5 and such binding results in the inhibition of the phosphorylation of Thr75-DARPP-32 and wherein said agent can cross the blood brain barrier.

2. A method for treating drug abuse in an individual comprising administration to the individual an agent that is a member of a compound selected from the group consisting of an indirubin and a paullone, wherein said agent binds to Cdk5 and such binding results in the inhibition of the phosphorylation of Thr75-DARPP-32 and wherein said agent can cross the blood brain barrier.

* * * * *

SEQUENCE LISTING

```
<160> NUMBER OF SEQ ID NOS: 5

<210> SEQ ID NO 1
<211> LENGTH: 204
<212> TYPE: PRT
<213> ORGANISM: Homo sapiens

<400> SEQUENCE: 1

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Asn Glu Asn Gln Ala Ser Glu Glu Glu Asp Glu Leu Gly Glu Leu Arg
            100                 105                 110

Glu Leu Gly Tyr Pro Arg Glu Glu Asp Glu Glu Glu Glu Glu Asp Asp
        115                 120                 125

Glu Glu Glu Glu Glu Glu Glu Asp Ser Gln Ala Glu Val Leu Lys Val
    130                 135                 140

Ile Arg Gln Ser Ala Gly Gln Lys Thr Thr Arg Gly Leu Gly Leu Glu
145                 150                 155                 160

Gly Pro Trp Glu Arg Pro Pro Pro Leu Asp Glu Ser Glu Arg Asp Gly
                165                 170                 175

Gly Ser Glu Asp Gln Val Glu Asp Pro Ala Leu Ser Glu Pro Gly Glu
            180                 185                 190

Glu Pro Gln Arg Pro Ser Pro Ser Glu Pro Gly Arg
        195                 200


<210> SEQ ID NO 2
<211> LENGTH: 201
<212> TYPE: PRT
<213> ORGANISM: Mus musculus

<400> SEQUENCE: 2

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Glu Glu Glu Ala Ser Pro His Gln Arg Thr Ser Gly Glu Gly
    50                  55                  60
```

-continued

```
His His Pro Lys Ser Lys Arg Pro Asn Pro Cys Ala Tyr Thr Pro Pro
65                  70                  75                  80

Ser Leu Lys Ala Val Arg Arg Leu Gln Thr Ile Ser Asn Leu Ser Glu
                85                  90                  95

Asn Gln Ala Ser Glu Glu Glu Asp Glu Leu Gly Glu Leu Arg Glu Leu
            100                 105                 110

Gly Tyr Pro Gln Glu Asp Asp Glu Glu Asp Glu Asp Glu Glu Glu Asp
        115                 120                 125

Glu Glu Glu Asp Ser Gln Ala Glu Val Leu Lys Gly Ser Arg Gly Thr
    130                 135                 140

Val Gly Gln Lys Leu Leu Val Ala Gly Val Trp Arg Gly Pro Gly Ser
145                 150                 155                 160

Ala His Leu Leu Trp Met Ser Pro Arg Glu Met Glu Thr Leu Arg Thr
                165                 170                 175

Lys Trp Lys Ala Glu Gln His Glx Val Ser Leu Glu Arg Asn Leu Ser
            180                 185                 190

Ile Pro Ala Pro Pro Glu Pro Gly Thr
        195                 200


<210> SEQ ID NO 3
<211> LENGTH: 205
<212> TYPE: PRT
<213> ORGANISM: Rattus sp.

<400> SEQUENCE: 3

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Ser Ser Pro His Gln Arg Thr Ser Gly Glu Gly His His Pro
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Thr Ile Ser Asn Leu
                85                  90                  95

Ser Glu Asn Gln Ala Ser Glu Glu Glu Asp Glu Leu Gly Glu Leu Arg
            100                 105                 110

Glu Leu Gly Tyr Pro Gln Glu Asp Asp Glu Glu Asp Glu Asp Glu Asp
        115                 120                 125

Glu Glu Glu Asp Glu Glu Glu Asp Ser Gln Ala Glu Val Leu Lys Gly
    130                 135                 140

Ser Arg Gly Thr Ala Gly Gln Lys Leu Thr Ser Gly Gln Gly Leu Glu
145                 150                 155                 160

Gly Pro Trp Glu Arg Pro Pro Pro Leu Asp Glu Pro Gln Arg Asp Gly
                165                 170                 175

Asn Ser Glu Asp Gln Gly Glu Gly Arg Ala Thr Gln Ser Glu Pro Gly
            180                 185                 190

Glu Glu Pro Arg His Pro Thr Pro Pro Glu Ser Gly Thr
        195                 200                 205


<210> SEQ ID NO 4
<211> LENGTH: 203
<212> TYPE: PRT
<213> ORGANISM: bovine
```

-continued

```
<400> SEQUENCE: 4

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Gly Glu Asn Gln Ala Ser Glu Glu Glu Asp Glu Leu Gly Glu Leu Arg
            100                 105                 110

Glu Leu Gly Tyr Pro Arg Glu Glu Glu Glu Glu Glu Glu Glu Glu Asp
        115                 120                 125

Glu Glu Glu Glu Glu Asp Ser Gln Ala Glu Val Leu Lys Gly Ser Arg
    130                 135                 140

Gly Ser Ala Gly Gln Lys Thr Thr Tyr Gly Gln Gly Leu Glu Gly Pro
145                 150                 155                 160

Trp Glu Arg Pro Pro Pro Leu Asp Gly Pro Gln Arg Asp Gly Ser Ser
                165                 170                 175

Glu Asp Gln Val Glu Asp Pro Ala Leu Asn Glu Pro Gly Glu Glu Pro
            180                 185                 190

Gln Arg Met Pro Ala His Pro Glu Pro Gly Thr
        195                 200


<210> SEQ ID NO 5
<211> LENGTH: 9
<212> TYPE: PRT
<213> ORGANISM: artificial sequence
<220> FEATURE:
<223> OTHER INFORMATION: a peptide used as an antigen

<400> SEQUENCE: 5

Cys Ala Tyr Thr Pro Pro Ser Leu Lys
1               5
```